United States Patent [19]

Baasner et al.

[11] Patent Number: 5,994,389
[45] Date of Patent: *Nov. 30, 1999

[54] N-ARYL- AND N-ALKYLSULFONYLAMINALS

[75] Inventors: Bernd Baasner, Bergisch Gladbach; Hermann Hagemann, Leverkusen; Markus Heil, Leverkusen; Folker Lieb, Leverkusen; Hermann Uhr, Krefeld; Christoph Erdelen, Leichlingen, all of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/915,999

[22] Filed: Aug. 21, 1997

Related U.S. Application Data

[62] Division of application No. 08/716,255, Sep. 13, 1996, Pat. No. 5,726,199.

[30]  Foreign Application Priority Data

Mar. 21, 1994 [DE] Germany .............................. 44 09 577
Apr. 20, 1994 [DE] Germany .............................. 44 13 659

[51] Int. Cl.⁶ ........................ A01N 43/46; C07D 405/04; C07D 207/34; C07D 207/42
[52] U.S. Cl. .......................... 514/422; 514/427; 548/526; 548/561
[58] Field of Search ................... 548/526, 561; 514/422, 427

[56]  References Cited

U.S. PATENT DOCUMENTS 5,130,328  7/1992  Kameswaran .
5,192,794  3/1993  Uhr et al. ................. 514/422
5,280,021  1/1994  Kuhn et al. .
5,310,747  5/1994  Enomoto et al. .
5,510,364  4/1996  Lunkenheimer et al. .
5,521,211  5/1996  Uhr et al. ................. 514/426

FOREIGN PATENT DOCUMENTS 0 515 941  12/1992  European Pat. Off. .
0 545 103   6/1993  European Pat. Off. .
42 37 548   5/1994  Germany .
42 37 557   5/1994  Germany .
WO 92 13451 8/1992  WIPO .
WO 93 24001 12/1993 WIPO .

OTHER PUBLICATIONS

Cram & Hammond, "Organic Chemistry," McGraw–Hill Book Co., NY (1964) 2nd Ed., pp. 565–567.

*Primary Examiner*—Patricia L. Morris
*Attorney, Agent, or Firm*—Sprung Kramer Schaefer & Briscoe

[57]  ABSTRACT

The invention relates to novel substituted N-aryl- and N-alkylsulfonylaminals of the formula (I)

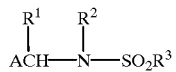

in which

A represents specific N-heterocycles specified in the description and $R^1$, $R^2$ and $R^3$ have the meaning given in the description, to a process for their preparation and to their use as agents for combating pests.

5 Claims, No Drawings

N-ARYL- AND N-ALKYLSULFONYLAMINALS

This is a divisional application of Ser. No. 08/716,255, filed Sep. 19, 1996, now U.S. Pat. No. 5,726,199, which is a 371 of PCT/EP95/00853.

The invention relates to novel substituted N-aryl- and N-alkylsulfonylaminals, to processes for their preparation and their use as agents for combating pests.

It is known that certain imidazoles and pyrroles such as, for example, 2,4-bis-trifluoromethyl-3-bromo-2-(4-chlorophenyl)-pyrrole have insecticidal properties (cf. e.g. JP 6 293 279 and EP 0 481 182).

However, the activity of these previously known compounds is not completely satisfactory in all areas of application, especially at low application rates and concentrations.

Novel N-aryl- and N-alkylsulfonylaminals have been found of the formula (I)

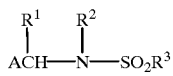

(I)

in which
R$^1$ represents hydrogen, represents optionally substituted alkyl or represents optionally substituted aryl,
R$^2$ and R$^3$ independently of one another represent optionally substituted alkyl or represent optionally substituted aryl, and
A a) represents a heterocyclic radical of the formula (II)

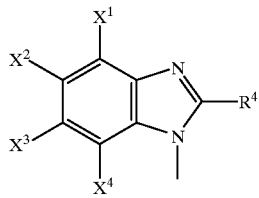

(II)

in which
R$^4$ represents fluoroalkyl and
X$^1$, X$^2$, X$^3$ and X$^4$ independently of one another in each case represent hydrogen, halogen, cyano or nitro, or represent in each case optionally substituted alkyl, alkoxy, alkylthio, alkylslfinyl, alkylsulfonyl or cycloalkyl, represent optionally substituted, fused-on dioxyalkylene, represent hydroxycarbonyl, alkylcarbonyl, alkoxycarbonyl orcycloalkyloxycarbonyl, represent in each case optionally substituted amino or aminocarbonyl, or represent in each case optionally substituted aryl, aryloxy, arylthio, arylsulfinyl, arylsulfonyl, arylsulfonyloxy, arylcarbonyl, aryloxycarbonyl, arylazo or arylthiomethylsulfonyl, or
b) represents a heterocyclic radical of the formula (III)

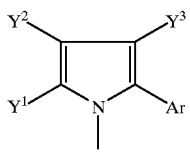

(III)

in which
Ar represents optionally substituted phenyl, pyridyl or naphthyl and

Y$^1$, Y$^2$ and Y$^3$ independently of one another represent hydrogen, optionally substituted alkyl, cyano, nitro or halogen, represent optionally substituted alkylthio, represent optionally substituted alkylsulfinyl or represent optionally substituted allylsulfonyl, or
c) represents a heterocyclic radical of the formula (IV)

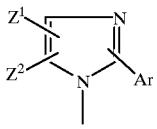

(IV)

in which
Ar has the meaning given above,
Z$^1$ represents halogen, optionally substituted alkyl, optionally substituted aryl, or nitro, represents optionally substituted alkylthio, represents optionally substituted alkylsulfinyl or represents optionally substituted alkylsulfonyl, or cyano, and
Z$^2$ represents optionally substituted alkyl, or
d) represents a heterocyclic radical of the formula (V)

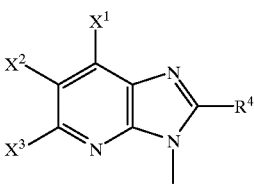

(V)

in which
X$^1$, X$^2$, X$^3$ and R$^4$ have the meaning given above.

The inclusion of the various meanings of the group A results in the following principal structures (Ia), (Ib), (Ic) and (Id):

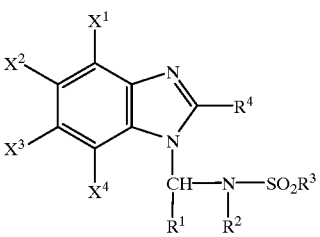

(Ia)

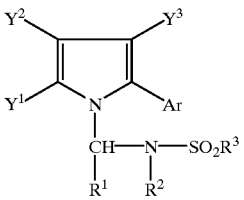

(Ib)

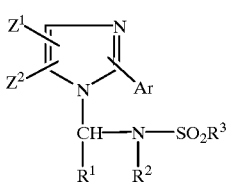

(Ic)

-continued

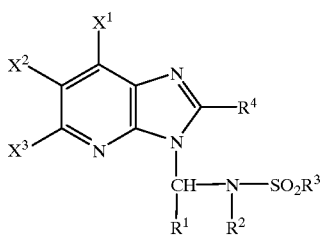

(Id)

in which

Ar, $R^1$, $R^2$, $R^3$, $R^4$, $X^1$, $X^2$, $X^3$, $X^4$, $Y^1$, $Y^2$, $Y^3$, $Z^1$ and $Z^2$ have the meanings given above.

The compounds of the formula (I) may if appropriate, depending on the nature and number of the substituents, be present as geometrical and/or optical isomers or regioisomers or their isomer mixtures in differing composition. Both the pure isomers and the isomer mixtures are claimed according to the invention.

In particular, the compounds of the formula (Ia) may be present as isomers, depending on which of the two nitrogen atoms in the imidazole ring carries the substituent.

The compounds of the formula (Ic) may be present as isomers in respect of the position of the substituents in positions 4 and 5.

Furthermore, it has been found that the novel substituted N-aryl- and N-alkylsulfonylaminals of the formula (I) are obtained by reacting heterocycles of the formula (VI)

HA (VI), in which

A has the meanings given above, with compounds of the formula (VII)

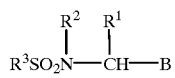

(VII)

in which $R^1$, $R^2$ and $R^3$ have the meanings given above and

B represents a suitable leaving group optionally in the presence of a diluent and optionally in the presence of a reaction auxiliary.

Finally it has been found that the novel substituted N-aryl- and N-alkysulfonylaminals of the formula (I) possess good activity against pests.

Surprisingly, the substituted N-aryl- and N-alkylsulfonylaminals of the formula (I) according to the invention display a considerably better activity against animal pests than the previously known compounds which are closest to them in terms of their constitution.

A general definition of the substituted N-aryl- and N-alkylsulfonylaminals according to the invention is given by the formula (I).

$R^1$ preferably represents hydrogen, represents straight-chain or branched alkyl having 1 to 8 carbon atoms or represents phenyl which is optionally monosubstituted or polysubstituted by identical or different substituents, suitable substituents being:

halogen, cyano, nitro, in each case straight-chain or branched alkyl, alkoxy, alkylthio, alkylsulfinyl or alkylsulfonyl having in each case 1 to 6 carbon atoms, in each case straight-chain or branched halogenoalkyl, halogenoalkoxy, halogenoalkylthio, halogenoalkylsulfinyl or halogenoalkylsulfonyl having in each case 1 to 6 carbon atoms and 1 to 13 identical or different halogen atoms, in each case straight-chain or branched alkoxyalkyl, alkoxyalkoxy, alkanoyl, alkoxycarbonyl or alkoxyiminoalkyl having in each case 1 to 6 carbon atoms in the individual alkyl moieties, divalent dioxyalkylene having 1 to 5 carbon atoms which is optionally monosubstituted or polysubstituted by identical or different substituents consisting of halogen and/or straight-chain or branched alkyl having 1 to 6 carbon atoms and/or straight-chain or branched halogenoalkyl having 1 to 6 carbon atoms and 1 to 13 identical or different halogen atoms, or phenyl which is optionally monosubstituted or polysubstituted by identical or different substituents consisting of halogen and/or straight-chain or branched alkyl having 1 to 6 carbon atoms and/or straight-chain or branched halogenoalkyl having 1 to 6 carbon atoms and 1 to 13 identical or different halogen atoms.

$R^2$ and $R^3$ independently of one another preferably represent straight-chain or branched alkyl having 1 to 8 carbon atoms or represent phenyl which is optionally monosubstituted or polysubstituted by identical or different substituents, suitable substituents being:

halogen, cyano, nitro, in each case straight-chain or branched alkyl, alkoxy, alkythio, aikylsulfinyl or alkylsulfonyl having in each case 1 to 6 carbon atoms, in each case straight-chain or branched halogenoalkyl, halogenoalkoxy, halogenoalkylthio, halogenoalkylsulfinyl or halogenoalkylsulfonyl having in each case 1 to 6 carbon atoms and 1 to 13 identical or different halogen atoms, in each case straight-chain or branched alkoxyalkyl, alkoxyalkoxy, alkanoyl, alkoxycarbonyl or alkoxyiminoalkyl having in each case 1 to 6 carbon atoms in the individual alkyl moieties, divalent dioxyalkylene having 1 to 5 carbon atoms which is optionally monosubstituted or polysubstituted by identical or different substituents consisting of halogen and/or straight-chain or branched alkyl having 1 to 6 carbon atoms and/or straight-chain or branched halogenoalkyl having 1 to 6 carbon atoms and 1 to 13 identical or different halogen atoms, or phenyl which is optionally monosubstituted or polysubstituted by identical or different substituents consisting of halogen and/or straight-chain or branched alkyl having 1 to 6 carbon atoms and/or straight-chain or branched halogenoalkyl having 1 to 6 carbon atoms and 1 to 13 identical or different halogen atoms.

$R^4$ preferably represents perfluoroalkyl or partially fluorinated alkyl having in each case 1 to 25 carbon atoms and up to 50 fluorine atoms.

$X^1$, $X^2$, $X^3$ and $X^4$ independently of one another preferably in each case represent hydrogen, fluorine, chlorine, bromine, iodine, cyano or nitro, represent in each case straight-chain or branched alkyl, alkoxy, alkylthio, alkylsulfinyl or alkylsulfonyl having in each case 1 to 8 carbon atoms, represent cycloalkyl having 3 to 8 carbon atoms, represent in each case straight-chain or branched halogenoalkyl, halogenoalkoxy, halogenoalkylthio, halogenoalkylsulfinyl, halogenoalkylsulfonyl having in each case 1 to 6 carbon atoms and 1 to 13 identical or different halogen atoms, or represent divalent dioxyalkylene having 1 to 5 carbon atoms which is optionally monosubstituted or polysubstituted by identical or different substituents consisting of halogen and/or straight-chain or branched alkyl having 1 to 4 carbon atoms and/or straight-chain or branched halogenoalkyl having 1 to 4 carbon atoms and 1 to 9 identical or different halogen atoms, or furthermore represent hydroxycarbonyl, represent in each case straight-chain or branched alkylcarbonyl or alkoxycarbonyl having in each case 1 to 6 carbon atoms in the alkyl moiety, represent cycloalkyloxycarbonyl having 3 to 8 carbon atoms in the cycloalkyl moiety, or represent amino or aminocarbonyl each of which is optionally monosubstituted or polysubstituted by identical or different substituents, suitable substituents for amino being in each case:

in each case straight-chain or branched alkyl having 1 to 6 carbon atoms, halogenoalkyl having 1 to 6 carbon atoms and 1 to 13 halogen atoms, alkoxyalkyl or alkylcarbonyl having in each case 1 to 6 carbon atoms in the individual alkyl moieties, or arylcarbonyl, arylsulfonyl, arylaminocarbonyl or arylmethylsulfonyl having in each case 1 to 6 carbon atoms in the aryl moiety, each of which is optionally monosubstituted or polysubstituted in the aryl moiety by identical or different substituents, suitable substituents for aryl being in each case those mentioned as preferable in the case of $R^1$;

or furthermore represent aryl, aryloxy, arylthio, arylsulfnyl, arylsulfonyl, arylsulfonyloxy, arylcarbonyl, aryloxycarbonyl, arylthiomethylsulfonyl or arylazo having in each case 6 to 10 carbon atoms in the aryl moiety, each of which is optionally monosubstituted or polysubstituted in the aryl moiety by identical or different substituents, suitable substituents for aryl being in each case those mentioned as preferable in the case of $R^1$.

Ar preferably represents phenyl which is optionally monosubstituted to pentasubstituted by identical or different substituents consisting of halogen, $C_1$–$C_8$-alkyl, $C_2$–$C_8$-alkenyl, and $C_2$–$C_8$-alkinyl, the alkyl, alkenyl or alkinyl radicals being optionally substituted by 1 to 6 radicals from the halogen series, or $C_1$–$C_5$-alkoxy which is optionally substituted by 1 to 6 halogen atoms, or $C_1$–$C_5$-thioalkyl which is optionally substituted by 1 to 6 radicals from the halogen series, or ($C_1$–$C_5$-alkyl)carbonyloxy, or divalent dioxyalkylene having 1 to 5 carbon atoms which is optionally substituted by $C_1$–$C_8$-alkoxy, $C_2$–$C_8$-alkenoxy or $C_2$–$C_5$-alkinoxy, the alkoxy, alkenoxy or alkinoxy radicals being optionally substituted by 1 to 6 halogen atoms, or by $C_1$–$C_8$-thioalkyl, $C_2$–$C_8$-thioalkenyl or $C_2$–$C_8$-thioalkinyl, the thioalkyl, thioalkenyl or thioalkinyl radicals being optionally substituted by 1 to 6 halogen atoms, or by ($C_1$–$C_8$-alkyl)carbonyloxy which is optionally substituted by 1 to 6 halogen atoms, or by amino which is optionally substituted by 1 or 2 identical or different alkyl radicals having 1 to 8 carbon atoms, which are optionally substituted by 1 to 6 halogen atoms, or by nitro or cyano, or by 1 to 9 identical or different halogen atoms, or represents pyridyl which is optionally monosubstituted to tetrasubstituted by identical or different halogen substituents.

$Y^1$, $Y^2$ and $Y^3$ independently of one another preferably represent hydrogen, halogen, cyano, or nitro, represent $C_1$–$C_6$-alkyl which is optionally substituted by 1 to 8 identical or different halogen atoms, or represent $C_1$–$C_6$-alkylthio which is optionally substituted by halogen, represent $C_1$–$C_6$-alkylsulfinyl which is optionally substituted by halogen or represent $C_1$–$C_6$-alkylsulfonyl which is optionally substituted by halogen.

$Z^1$ preferably represents halogen, represents nitro, represents $C_1$–$C_6$-alkyl which is optionally substituted by 1 to 13 identical or different halogen atoms, represents $C_1$–$C_6$-alkylthio which is optionally substituted by halogen, represents $C_1$–$C_6$-alkylsulfinyl which is optionally substituted by halogen, represents $C_1$–$C_6$-alkylsulfonyl which is optionally substituted by halogen, or represents cyano.

$Z^2$ preferably represents $C_1$–$C_6$-alkyl which is optionally substituted by 1 to 13 identical or different halogen atoms.

$R^1$ particularly preferably represents hydrogen, represents straight-chain or branched alkyl having 1 to 6 carbon atoms or represents phenyl which is optionally monosubstituted or polysubstituted by identical or different substituents, suitable substituents being:

halogen, cyano, nitro, in each case straight-chain or branched ally, alkoxy, alkylthio, alkylsulfinyl or alkylsulfonyl having in each case 1 to 4 carbon atoms, in each case straight-chain or branched halogenoalkyl, halogenoalkoxy, halogenoalkylthio, halogenoalkylsulfinyl or halogenoalkylsulfonyl having in each case 1 to 4 carbon atoms and 1 to 9 identical or different halogen atoms, in each case straight-chain or branched alkoxyalkyl, alkoxyalkoxy, alkanoyl, alkoxycarbonyl or alkoxyiminoalkyl having in each case 1 to 4 carbon atoms in the individual alkyl moieties, divalent dioxyalkyene having 1 to 4 carbon atoms which is optionally monosubstituted to hexasubstituted by identical or different substituents consisting of halogen and/or straight-chain or branched alkyl having 1 to 4 carbon atoms and/or straight-chain or branched halogenoalkyl having 1 to 4 carbon atoms and 1 to 9 identical or different halogen atoms, or phenyl which is optionally monosubstituted to pentasubstituted by identical or different substituents consisting of halogen and/or straight-chain or branched alkyl having 1 to 4 carbon atoms and/or straight-chain or branched halogenoalkyl having 1 to 4 carbon atoms and 1 to 9 identical or different halogen atoms.

$R^2$ and $R^3$ independently of one another particularly preferably represent straight-chain or branched alkyl having 1 to 6 carbon atoms or represent phenyl which is optionally monosubstituted to trisubstituted by identical or different substituents, suitable substituents being:

halogen, cyano, nitro, in each case straight-chain or branched alkyl, alkoxy, alkylthio, alkylsulfinyl or alkylsulfonyl having in each case 1 to 4 carbon atoms, in each case straight-chain or branched halogenoalkyl, halogenoalkoxy, halogenoalkylthio, halogenoalkylsulfinyl or halogenoalkylsulfonyl having in each case 1 to 4 carbon atoms and 1 to 9 identical or different halogen atoms, in each case straight-chain or branched alkoxyalkyl, alkoxyalkoxy, alkanoyl, alkoxycarbonyl or alkoxyiminoalkyl having in each case 1 to 4 carbon atoms in the individual alkyl moieties, divalent dioxyalkylene having 1 to 4 carbon atoms which is optionally monosubstituted to hexasubstituted by identical or different substituents consisting of halogen and/or straight-chain or branched alkyl having 1 to 4 carbon atoms and/or straight-chain or branched halogenoalkyl having 1 to 4 carbon atoms and 1 to 9 identical or different halogen atoms, or phenyl which is optionally monosubstituted to pentasubstituted by identical or different substituents consisting of halogen and/or straight-chain or branched alkyl having 1 to 4 carbon atoms and/or straight-chain or branched halogenoalkyl having 1 to 4 carbon atoms and 1 to 9 identical or different halogen atoms.

$R^4$ particularly preferably represents $CF_3$, $C_2F_5$, $C_3F_7$, $CHF_2$ or $CH_2F$.

$X^1$, $X^2$, $X^3$ and $X^4$ independently of one another particularly preferably represent in each case hydrogen, fluorine, chlorine, bromine, iodine, cyano or nitro, represent in each case straight-chain or branched alkyl, alkoxy, alkylthio, alkylsulfinyl or alkylsulfonyl having in each case 1 to 6 carbon atoms, represent cycloalkyl having 3 to 7 carbon atoms, represent in each case straight-chain or branched halogenoalkyl, halogenoalkoxy, halogenoalkylthio, halogenoalkylsulfinyl, halogenoalkylsulfonyl, having in each case 1 to 4 carbon atoms and 1 to 9 identical or different halogen atoms, or represent divalent dioxyalkylene having 1 to 4 carbon atoms which is optionally monosubstituted to hexasubstituted by identical or different substituents consisting of halogen and/or straight-chain or branched alkyl having 1 to 4 carbon atoms and/or straight-chain or branched halogenoalkyl having 1 to 4 carbon atoms and 1 to 9 identical or different halogen atoms, or furthermore represents hydroxycarbonyl, represents in each case straight-chain or branched alkylcarbonyl or alkoxycarbonyl having in each case 1 to 4 carbon atoms in the alkyl moiety, represents cycloalkyloxycarbonyl having 3 to 7 carbon atoms in the cycloalkyl moiety, or represents amino or aminocarbonyl each of which is optionally monosubstituted or disubstituted by identical or different substituents, suitable substituents for amino being in each case:

in each case straight-chain or branched alkyl having 1 to 4 carbon atoms, halogenoalkyl having 1 to 4 carbon atoms and 1 to 9 halogen atoms, alkoxyalkyl or alkylcarbonyl having in each case 1 to 4 carbon atoms in the individual alkyl moieties, or arylcarbonyl, arylsulfonyl, arylaminocarbonyl or arylmethylsulfonyl having in each case 6 to 10 carbon atoms in the aryl moiety, each of which is optionally monosubstituted to pentasubstituted in the aryl moiety by identical or different substituents, suitable substituents for aryl being in each case those mentioned as particularly preferable in the case of $R^1$;

or furthermore represent aryl, aryloxy, arylthio, arylsulfinyl, arylsulfonyl, arylsulfonyloxy, arylcarbonyl, aryloxycarbonyl, arylthiomethylsulfonyl or arylazo having in each case 6 to 10 carbon atoms in the aryl moiety, each of which is optionally monosubstituted to pentasubstituted in the aryl moiety by identical or different substituents, suitable substituents for aryl being in each case those mentioned as particularly preferable in the case of $R^1$.

Ar particularly preferably represents phenyl which is optionally monosubstituted to tetrasubstituted by identical or different substituents consisting of fluorine, chlorine or bromine, $C_1$–$C_6$-alkyl, $C_2$–$C_6$-alkenyl and $C_2$–$C_6$-alkinyl, the alkyl, alkenyl or alkinyl radicals being optionally substituted by 1 to 5 fluorine and/or chlorine atoms, or $C_1$–$C_4$-alkoxy which is optionally substituted by 1 to 5 fluorine and/or chlorine atoms, or $C_1$–$C_4$-thioalkyl which is optionally substituted by 1 to 5 fluorine and/or chlorine atoms, or $C_1$–$C_4$-acyloxy, or divalent dioxyalkylene having 1 to 4 carbon atoms which is optionally substituted by $C_1$–$C_6$-alkoxy, $C_2$–$C_6$-alkenoxy or $C_2$–$C_6$-alkinoxy, the alkoxy, alkenoxy or alkinoxy radicals being optionally substituted by 1 to 5 fluorine and/or chlorine atoms, or by $C_1$–$C_6$-thioalkyl, $C_2$–$C_6$-thioalkenyl or $C_2$–$C_6$-thioalkinyl, the thioalkyl, thioalkenyl or thioalkinyl radicals being optionally substituted by 1 to 5 fluorine and/or chlorine atoms, or by ($C_1$–$C_8$alkyl)carbonyloxy which is optionally substituted by 1 to 5 fluorine and/or chlorine atoms, or by amino which is optionally substituted by 1 to 2 identical or different alkyl radicals having 1 to 6 carbon atoms, which are optionally substituted by 1 to 5 fluorine and/or chlorine atoms, or by nitro or cyano, or by 1 to 7 identical or different halogen atoms, or represents pyridyl which is optionally monosubstituted to tetrasubstituted by identical or different halogen substituents.

$Y^1$, $Y^2$ and $Y^3$ independently of one another particularly preferably represent hydrogen, halogen, cyano or nitro, represent $C_1$–$C_5$-alkyl which is optionally substituted by 1 to 6 identical or different halogen atoms, or represent $C_1$–$C_5$-alkylthio which is optionally substituted by halogen, represent $C_1$–$C_5$-alkylsulfinyl which is optionally substituted by halogen or represent $C_1$–$C_5$-alkylsulfonyl which is optionally substituted by halogen.

$Z^1$ particularly preferably represents halogen, represents $C_1$–$C_5$-alkyl which is optionally substituted by 1 to 11 identical or different halogen atoms, represents nitro, represents $C_1$–$C_5$-alkylthio which is optionally substituted by halogen, represents $C_1$–$C_5$-alkylsulfinyl which is optionally substituted by halogen, represents $C_1$–$C_5$-alkylsulfonyl which is optionally substituted by halogen, or represents cyano.

$Z^2$ particularly preferably represents $C_1$–$C_5$-alkyl which is optionally substituted by 1 to 11 identical or different halogen atoms.

$R^1$ very particularly preferably represents straight-chain or branched alkyl having 1 to 4 carbon atoms or represents phenyl which is optionally monosubstituted or disubstituted by identical or different substituents, suitable substituents being:

halogen, cyano, nitro, in each case straight-chain or branched alkyl, alkoxy, alkylthio, alkylsulfinyl or alkylsulfonyl having in each case 1 to 3 carbon atoms, in each case straight-chain or branched halogenoalkyl, halogenoalkoxy, halogenoalkylthio, halogenoalkylsulfinyl or halogenoalkylsulfonyl having in each case 1 to 3 carbon atoms and 1 to 7 identical or different halogen atoms, in each case straight-chain or branched alkoxyalkyl, alkoxyalkoxy, alkanoyl, alkoxycarbonyl or alkoxyiminoalkyl having in each case 1 to 3 carbon atoms in the individual alkyl moieties, divalent dioxyalkylene having 1 to 3 carbon atoms which is optionally monosubstituted to tetrasubstituted by identical or different substituents consisting of halogen and/or straight-chain or branched alkyl having 1 to 3 carbon atoms and/or straight-chain or branched halogenoalkyl having 1 to 3 carbon atoms and 1 to 7 identical or different halogen atoms, or phenyl which is optionally monosubstituted to trisubstituted by identical or different substituents consisting of halogen and/or straight-chain or branched alkyl having 1 to 3 carbon atoms and/or straight-chain or branched halogenoalkyl having 1 to 3 carbon atoms and 1 to 7 identical or different halogen atoms.

$R^2$ and $R^3$ independently of one another very particularly preferably represent straight-chain or branched alkyl having 1 to 4 carbon atoms or represent phenyl which is optionally monosubstituted or disubstituted by identical or different substituents, suitable substituents being:

halogen, cyano, nitro, in each case straight-chain or branched alkyl, alkoxy, alkylthio, alkylsulfinyl or alkylsulfonyl having in each case 1 to 3 carbon atoms, in each case straight-chain or branched halogenoalkyl, halogenoalkoxy, halogenoalkylthio, halogenoalkylsulfinyl or halogenoalkylsulfonyl having in each case 1 to 3 carbon atoms and 1 to 7 identical or different halogen atoms, in each case straight-chain or branched alkoxyalkyl, alkoxyalkoxy, alkanoyl, alkoxycarbonyl or alkoxyiminoalkyl having in each case 1 to 3 carbon atoms in the individual alkyl moieties, divalent dioxyalkylene having 1 to 3 carbon atoms which is optionally monosubstituted to tetrasubstituted by identical or different substituents consisting of halogen and/or straight-chain or branched alkyl having 1 to 3 carbon atoms and/or straight-chain or branched halogenoalkyl having 1 to 3 carbon atoms and 1 to 7 identical or different halogen atoms, or phenyl which is optionally monosubstituted to trisubstituted by identical or different substituents consisting of halogen and/or straight-chain or branched alkyl having 1 to 3 carbon atoms and/or straight-chain or branched halogenoalkyl having 1 to 3 carbon atoms and 1 to 7 identical or different halogen atoms.

$R^4$ very particularly preferably represents $CF_3$, $C_2F_5$ or $CHF_2$.

$X^1$, $X^2$, $X^3$ and $X^4$ independently of one another very particularly preferably each represent hydrogen, fluorine, chlorine, bromine, cyano or nitro, represent in each case straight-chain or branched alkyl, alkoxy, alkylthio, alkylsulfinyl or alkylsulfonyl having in each case 1 to 4 carbon atoms, represent cycloalkyl having 3, 5 or 6 carbon atoms, represent in each case straight-chain or branched halogenoalkyl, halogenoalkoxy, halogenoalkylthio, halogenoalkylsulfinyl or halogenoalkylsulfonyl, having in each case 1 to 3 carbon atoms and 1 to 7 identical or different halogen atoms, or represent divalent dioxyalkylene having 1 to 3 carbon atoms which is optionally monosubstituted to tetrasubstituted by identical or different substituents consisting of halogen and/or straight-chain or branched alkyl having 1 to 3 carbon atoms and/or straight-chain or branched halogenoallyl having 1 to 3 carbon atoms and 1 to 7 identical or different halogen atoms, or furthermore represent hydroxycarbonyl, represent in each case straight-chain or branched alkylcarbonyl or alkoxycarbonyl having in each case 1 to 3 carbon atoms in the alkyl moiety, represent cycloalkyloxycarbonyl having 3, 5 or 6 carbon atoms in the cycloalkyl moiety, or represent amino or aminocarbonyl each of which is optionally monosubstituted or disubstituted by identical or different substituents, suitable substituents for amino being in each case:

in each case straight-chain or branched alkyl having 1 to 3 carbon atoms, halogenoalkyl having 1 to 3 carbon atoms and 1 to 7 halogen atoms, alkoxyalkyl or alkylcarbonyl having in each case 1 to 3 carbon atoms in the individual alkyl moieties, or phenylcarbonyl, phenylsulfonyl, phenylaminocarbonyl or phenylmethylsulfonyl, each of which is optionally monosubstituted to trisubstituted in the phenyl moiety by identical or different substituents, suitable substituents for phenyl being in each case those mentioned as very particularly preferable in the case of $R^1$;

or furthermore represent phenyl, phenyloxy, phenylthio, phenylsulfinyl, phenylsulfonyl, phenylsulfonyloxy, phenylcarbonyl, phenyloxycarbonyl, phenylthiomethylsulfonyl or phenylazo, each of which is optionally monosubstituted to trisubstituted in the phenyl moiety by identical or different substituents, suitable substituents for phenyl being in each case those mentioned as very particularly preferable in the case of $R^1$.

Ar very particularly preferably represents phenyl which is optionally monosubstituted to tetrasubstituted by identical or different substituents consisting of fluorine, chlorine or bromine, $C_1-C_4$-alkyl, $C_2-C_6$-alkenyl and $C_2-C_6$-alkinyl, the alkyl, alkenyl or alkinyl radicals being optionally substituted by 1 to 5 fluorine and/or chlorine atoms, $C_1-C_4$-alkoxy which is optionally substituted by 1 to 5 fluorine and/or chlorine atoms, $C_1-C_4$-thioalkyl which is optionally substituted by 1 to 5 fluorine and/or chlorine atoms, $C_1-C_4$-acyloxy, divalent dioxyalkylene having 1 to 3 carbon atoms which is substituted by $C_1-C_6$-alkoxy, $C_2-C_6$-alkenoxy or $C_2-C_6$-alkinoxy, the alkoxy, alkenoxy or alkinoxy radicals being optionally substituted by 1 to 5 fluorine and/or chlorine atoms, or by $C_1-C_4$-thioalkyl, $C_2-C_6$-thioalkenyl or $C_2-C_6$-thioalkinyl, the thioalkyl, thioalkenyl or thioalkinyl radicals being optionally substituted by 1 to 5 fluorine and/or chlorine atoms, or by ($C_1-C_5$-alkyl)carbonyloxy which is optionally substituted by 1 to 5 fluorine and/or chlorine atoms, or by amino which is optionally substituted by 1 or 2 identical or different alkyl radicals having 1 to 6 carbon atoms, which are optionally substituted by 1 to 5 fluorine and/or chlorine atoms, or by nitro or cyano, or by 1 to 5 identical or different halogen atoms, or represents pyridyl which is optionally monosubstituted to tetrasubstituted by identical or different halogen substituents.

$Y^1$, $Y^2$ and $Y^3$ independently of one another very particularly preferably represent hydrogen, halogen, cyano or nitro, represent $C_1-C_4$-alkyl which is optionally substituted by 1 to 6 identical or different halogen atoms, or represent $C_1-C_4$-alkylthio which is optionally substituted by halogen, represent $C_1-C_4$-alkylsulfinyl which is optionally substituted by halogen or represent $C_1-C_4$-alkylsulfonyl which is optionally substituted by halogen.

$Z^1$ very particularly preferably represents halogen, represents $C_1-C_4$-alkyl which is optionally substituted by 1 to 9 identical or different halogen atoms, represents nitro, represents $C_1-C_4$-alkylthio which is optionally substituted by halogen, represents $C_1-C_4$-alkylsulfinyl which is optionally substituted by halogen, represents $C_1-C_4$-alkylsulfonyl which is optionally substituted by halogen, or represents cyano.

$Z^2$ very particularly preferably represents $C_1-C_4$-alkyl which is optionally substituted by 1 to 9 identical or different halogen atoms.

The radical definitions and/or explanations listed above, given in general terms or in preferred ranges, can be combined with one another as desired, which thus includes combinations between the respective ranges and preferred ranges. They apply to the end products and, correspondingly, to the precursors and intermediates.

According to the invention, preference is given to the compounds of the formula (I) in which there is a combination of the meanings given above as being preferable.

According to the invention, particular preference is given to the compounds of the formula (I) in which there is a combination of the meanings given above as being particularly preferable.

According to the invention, very particular preference is given to the compounds of the formula (I) in which there is a combination of the meanings given above as being very particularly preferable.

Apart from the compounds mentioned in the Preparation Examples, specific mention may be made of the following N-aryl- and N-alkylsulfonylaminals of the formula (I). (Ph=Phenyl)

TABLE 1

(Ia)

| $R^1$ | $R^2$ | $R^3$ | $R^4$ | $X^1$ | $X^2$ | $X^3$ | $X^4$ |
|---|---|---|---|---|---|---|---|
| H | $CH_3$ | $CH_3$ | $CHF_2$ | H | Br | $CF_3$ | H |
| H | $CH_3$ | $CH_3$ | $CF_3$ | H | Br | $CF_3$ | H |
| H | $CH_3$ | $CH_3$ | $CF_3$ | Br | H | $CF_3$ | H |
| H | $CH_3$ | $CH_3$ | $CF_3$ | H | $OCF_2CF_2O$ | | H |
| H | $CH_3$ | $CH_3$ | $CF_3$ | H | $OCF_2O$ | | H |
| H | $CH_3$ | $CH_3$ | $CF_3$ | H | $CF_3$ | $CF_3$ | H |
| H | $CH_3$ | $CH_3$ | $CF_3$ | H | $CF_3O$ | $OCF_3$ | H |
| H | $CH_3$ | $CH_3$ | $CF_3$ | H | $OCF_3$ | H | H |
| H | $CH_3$ | $CH_3$ | $CF_3$ | H | $CH_3SO_2$ | H | H |
| H | $CH_3$ | $CH_3$ | $CF_3$ | H | $(C_2H_5)_2NCO$ | H | H |
| H | $CH_3$ | $CH_3$ | $CF_3$ | H | $CH_3OCO$ | H | H |
| H | $CH_3$ | $CH_3$ | $CF_3$ | H | $OCFClCF_2O$ | | H |
| H | $CH_3$ | $CH_3$ | $CF_3$ | H | $OCFClCFClO$ | | H |
| H | $CH_3$ | $CH_3$ | $CHF_2$ | H | $OCF_2CF_2O$ | | H |
| H | $CH_3$ | $CH_3$ | $CHF_2$ | H | $CF_3$ | $CF_3$ | H |
| H | $CH_3$ | $CH_3$ | $CHF_2$ | Br | H | $SCF_3$ | H |

TABLE 1-continued (Ia)

Structure: benzimidazole with X¹ (4-position), X² (5), X³ (6), X⁴ (7); N1 substituted with CH(R¹)-N(R²)-SO₂R³; 2-position has R⁴.

| R¹ | R² | R³ | R⁴ | X¹ | X² | X³ | X⁴ |
|---|---|---|---|---|---|---|---|
| H | CH₃ | CH₃ | CF₃ | Br | H | SCF₃ | H |
| H | CH₃ | CH₃ | CF₃ | Cl | H | SCF₃ | H |
| H | Ph | CH₃ | CHF₂ | H | Br | CF₃ | H |
| H | Ph | CH₃ | CHF₂ | H | OCF₂CF₂O | | H |
| H | Ph | CH₃ | CHF₂ | H | CF₃ | CF₃ | H |
| H | Ph | CH₃ | CHF₂ | Br | H | SCF₃ | H |
| H | Ph | CH₃ | CF₃ | H | Br | CF₃ | H |
| H | Ph | CH₃ | CF₃ | Br | H | CF₃ | H |
| H | Ph | CH₃ | CF₃ | Br | H | SCF₃ | H |
| H | Ph | CH₃ | CF₃ | H | OCFClCF₂O | | H |
| H | Ph | CH₃ | CF₃ | H | (C₂H₅)₂NCO | H | H |
| H | Ph | CH₃ | CF₃ | H | CH₃SO₂ | H | H |
| H | Ph | CH₃ | CF₃ | H | OCFClCFClO | | H |
| H | Ph | CH₃ | CF₃ | Cl | H | SCF₃ | H |
| H | Ph | CH₃ | CF₃ | H | OCF₃ | H | H |
| H | Ph | CH₃ | CF₃ | H | OCF₃ | OCF₃ | H |
| H | Ph | CH₃ | CF₃ | H | CF₃ | CF₃ | H |
| H | Ph | CH₃ | CF₃ | H | OCF₂O | | H |
| H | Ph | CH₃ | CF₃ | H | OCF₂CF₂O | | H |
| H | Ph | CH₃ | CF₃ | H | CH₃OCO | H | H |
| H | CH₃ | Ph | CF₃ | H | OCF₂CF₂O | | H |
| H | CH₃ | Ph | CF₃ | H | CF₃ | CF₃ | H |
| H | CH₃ | Ph | CF₃ | H | OCF₃ | H | H |
| H | CH₃ | Ph | CF₃ | H | OCFClCFClO | | H |
| H | CH₃ | Ph | CF₃ | H | OCF₂O | | H |
| H | CH₃ | Ph | CF₃ | H | OCF₃ | OCF₃ | H |
| H | CH₃ | Ph | CF₃ | Cl | H | SCF₃ | H |
| H | CH₃ | Ph | CHF₂ | H | Br | CF₃ | H |
| H | CH₃ | Ph | CHF₂ | H | OCF₂CF₂O | | H |
| H | CH₃ | Ph | CHF₂ | H | CF₃ | CF₃ | H |
| H | CH₃ | Ph | CHF₂ | Br | H | SCF₃ | H |
| H | CH₃ | Ph | CF₃ | H | CH₃SO₂ | H | H |
| H | CH₃ | Ph | CF₃ | H | (C₂H₅)₂NCO | H | H |
| H | CH₃ | Ph | CF₃ | H | OCFClCF₂O | | H |
| H | CH₃ | Ph | CF₃ | Br | H | SCF₃ | H |
| H | CH₃ | Ph | CF₃ | Br | H | CF₃ | H |
| H | CH₃ | Ph | CF₃ | H | Br | CF₃ | H |
| H | CH₃ | Ph | CF₃ | H | CH₃OCO | H | H |

TABLE 2

(Ib)

Structure: pyrrole with Y¹, Y², Y³ substituents and Ar group; N-substituted with CH(R¹)-N(R²)-SO₂R³.

| R¹ | R² | R³ | Ar | Y³ | Y² | Y¹ |
|---|---|---|---|---|---|---|
| H | CH₃ | CH₃ | 4-Cl-C₆H₄ | CN | Br | CF₃ |
| H | C₂H₅ | CH₃ | 4-Cl-C₆H₄ | CN | Br | CF₃ |

TABLE 2-continued
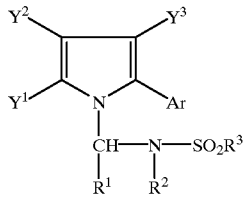
(Ib)
| R¹ | R² | R³ | Ar | Y³ | Y² | Y¹ |
|---|---|---|---|---|---|---|
| H | Ph | CH₃ |  | CN | Br | CF₃ |
| H | CH₃ | Ph |  | CN | Br | CF₃ |
| H | CH₃ | CH₃ | 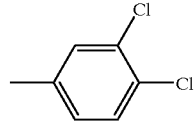 | CN | Br | CF₃ |
| H | CH₃ | CH₃ |  | CN | Br | CF₃ |
| H | CH₃ | CH₃ |  | CN | Br | CF₃ |
| H | CH₃ | CH₃ | 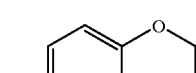 | CN | Br | CF₃ |
| H | C₂H₅ | CH₃ | 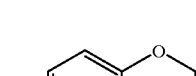 | CN | Br | CF₃ |
| H | CH₃ | CH₃ | 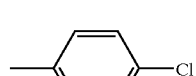 | CN | Br | C₂F₅ |
| H | C₂H₅ | CH₃ | 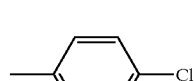 | CN | Br | C₂F₅ |

TABLE 2-continued
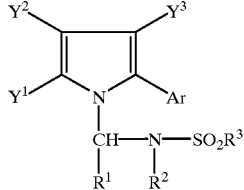
(Ib)
| R¹ | R² | R³ | Ar | Y³ | Y² | Y¹ |
|---|---|---|---|---|---|---|
| H | Ph | CH₃ | 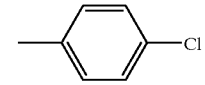 4-Cl-C₆H₄ | CN | Br | C₂F₅ |
| H | CH₃ | Ph | 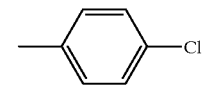 4-Cl-C₆H₄ | CN | Br | C₂F₅ |
| H | CH₃ | CH₃ | 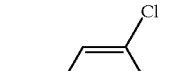 3,4-Cl₂-C₆H₃ | CN | Br | C₂F₅ |
| H | C₂H₅ | CH₃ |  3,4-Cl₂-C₆H₃ | CN | Br | C₂F₅ |
| H | CH₃ | CH₃ |  4-Cl-C₆H₄ | CN | Br | NO₂ |
| H | CH₃ | CH₃ |  3,4-Cl₂-C₆H₃ | CN | Br | NO₂ |
| H | CH₃ | CH₃ | 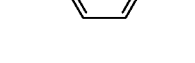 4-CF₃-C₆H₄ | CN | Br | NO₂ |
| H | CH₃ | CH₃ | 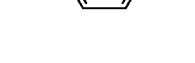 4-OCF₃-C₆H₄ | CN | Br | NO₂ |
| H | CH₃ | CH₃ |  | CN | Br | NO₂ |

TABLE 2-continued
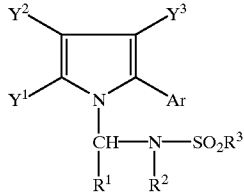
(Ib)
| R¹ | R² | R³ | Ar | Y³ | Y² | Y¹ |
|---|---|---|---|---|---|---|
| H | CH₃ | CH₃ | 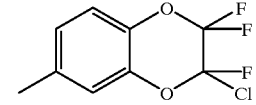 | CN | Cl | Cl |
| H | CH₃ | CH₃ | 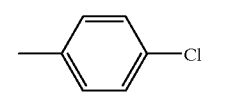 | CN | Br | Br |
| H | CH₃ | CH₃ | 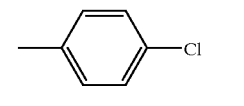 | CN | Cl | Cl |
| H | CH₃ | CH₃ | 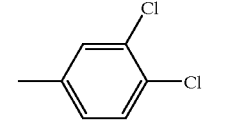 | CN | Br | Br |
| H | CH₃ | CH₃ | 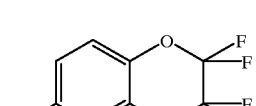 | CN | Br | Br |
| H | C₂H₅ | CH₃ | 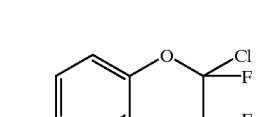 | CN | Br | Br |
| H | CH₃ | CH₃ | 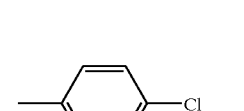 | Br | H | SO₂CCl₂F |
| H | CH₃ | CH₃ | 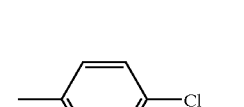 | Br | H | SO₂CClF₂ |
| H | CH₃ | CH₃ | 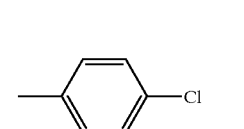 | Cl | Cl | SO₂CCl₂F |

TABLE 2-continued

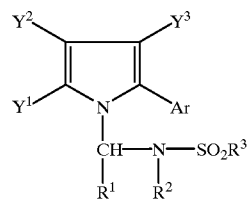

(Ib)

| R$^1$ | R$^2$ | R$^3$ | Ar | Y$^3$ | Y$^2$ | Y$^1$ |
|---|---|---|---|---|---|---|
| H | CH$_3$ | CH$_3$ | 3,4-diCl-C$_6$H$_3$ | Br | H | SO$_2$CCl$_2$F |
| H | CH$_3$ | CH$_3$ | 3,4-diCl-C$_6$H$_3$ | Br | H | SO$_2$CClF$_2$ |
| H | CH$_3$ | CH$_3$ | 4-CF$_3$-C$_6$H$_4$ | Br | H | SO$_2$CCl$_2$F |
| H | CH$_3$ | CH$_3$ | 4-Cl-C$_6$H$_4$ | Br | Br | SO$_2$CClF$_2$ |
| H | CH$_3$ | CH$_3$ | 3,4-diCl-C$_6$H$_3$ | Br | Br | SO$_2$CCl$_2$F |
| H | CH$_3$ | CH$_3$ | 4-F-C$_6$H$_4$ | Br | Br | SO$_2$CClF$_2$ |
| H | CH$_3$ | CH$_3$ | 2,4-diCl-C$_6$H$_3$ | Br | Br | SO$_2$CCl$_2$F |
| H | CH$_3$ | CH$_3$ | 4-Cl-C$_6$H$_4$ | NO$_2$ | Br | SO$_2$CClF$_2$ |
| H | CH$_3$ | CH$_3$ | 4-Cl-C$_6$H$_4$ | NO$_2$ | Br | SO$_2$CCl$_2$F |

TABLE 2-continued
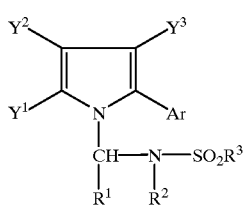
(Ib)
| $R^1$ | $R^2$ | $R^3$ | Ar | $Y^3$ | $Y^2$ | $Y^1$ |
|---|---|---|---|---|---|---|
| H | CH$_3$ | CH$_3$ | 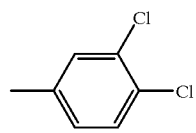 | NO$_2$ | Br | SO$_2$CClF$_2$ |
| H | CH$_3$ | CH$_3$ | 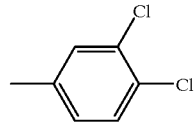 | NO$_2$ | Br | SO$_2$CCl$_2$F |
| H | CH$_3$ | CH$_3$ | 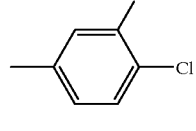 | CF$_3$ | CF$_3$ | CF$_3$ |
| H | C$_2$H$_5$ | CH$_3$ | 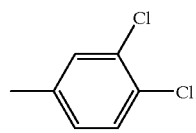 | CF$_3$ | CF$_3$ | CF$_3$ |
| H | CH$_3$ | Ph | 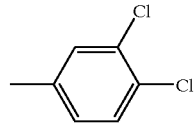 | CF$_3$ | CF$_3$ | CF$_3$ |
| H | CH$_3$ | CH$_3$ | 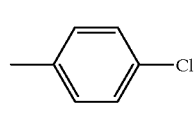 | CF$_3$ | CF$_3$ | CF$_3$ |
| H | C$_2$H$_5$ | CH$_3$ | 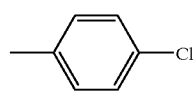 | CF$_3$ | CF$_3$ | CF$_3$ |

TABLE 3a (Ic-a)

Structure: imidazole ring with Z¹ and Z² substituents, N-substituted with Ar at 2-position, and CH(R¹)-N(R²)-SO₂R³ group on N.

| R¹ | R² | R³ | Ar | Z¹ | Z² |
|---|---|---|---|---|---|
| H | CH₃ | CH₃ | 4-Cl-C₆H₄ | Br | CF₃ |
| H | CH₃ | CH₃ | 3,4-Cl₂-C₆H₃ | Br | CF₃ |
| H | CH₃ | CH₃ | 2,4-Cl₂-C₆H₃ | Br | CF₃ |
| H | C₂H₅ | CH₃ | 4-CF₃-C₆H₄ | Br | CF₃ |
| H | CH₃ | Ph | 4-CF₃-C₆H₄ | Br | CF₃ |
| H | CH₃ | CH₃ | 4-OCF₃-C₆H₄ | Br | CF₃ |
| H | CH₃ | CH₃ | 2,2,3-trifluoro-3-chloro-benzodioxin-6-yl | Br | CF₃ |
| H | CH₃ | CH₃ | 2,2-difluoro-1,3-benzodioxol-5-yl | Br | CF₃ |
| H | CH₃ | CH₃ | 4-Cl-C₆H₄ | CF₃ | CF₃ |
| H | CH₃ | CH₃ | 3,4-Cl₂-C₆H₃ | CF₃ | CF₃ |
| H | CH₃ | CH₃ | 4-CF₃-C₆H₄ | CF₃ | CF₃ |
| H | CH₃ | CH₃ | 2,4-Cl₂-C₆H₃ | CF₃ | CF₃ |
| H | CH₃ | CH₃ | 4-Cl-C₆H₄ | NO₂ | CF₃ |
| H | CH₃ | CH₃ | 3,4-Cl₂-C₆H₃ | NO₂ | CF₃ |
| H | CH₃ | CH₃ | 4-CF₃-C₆H₄ | NO₂ | CF₃ |

TABLE 3b
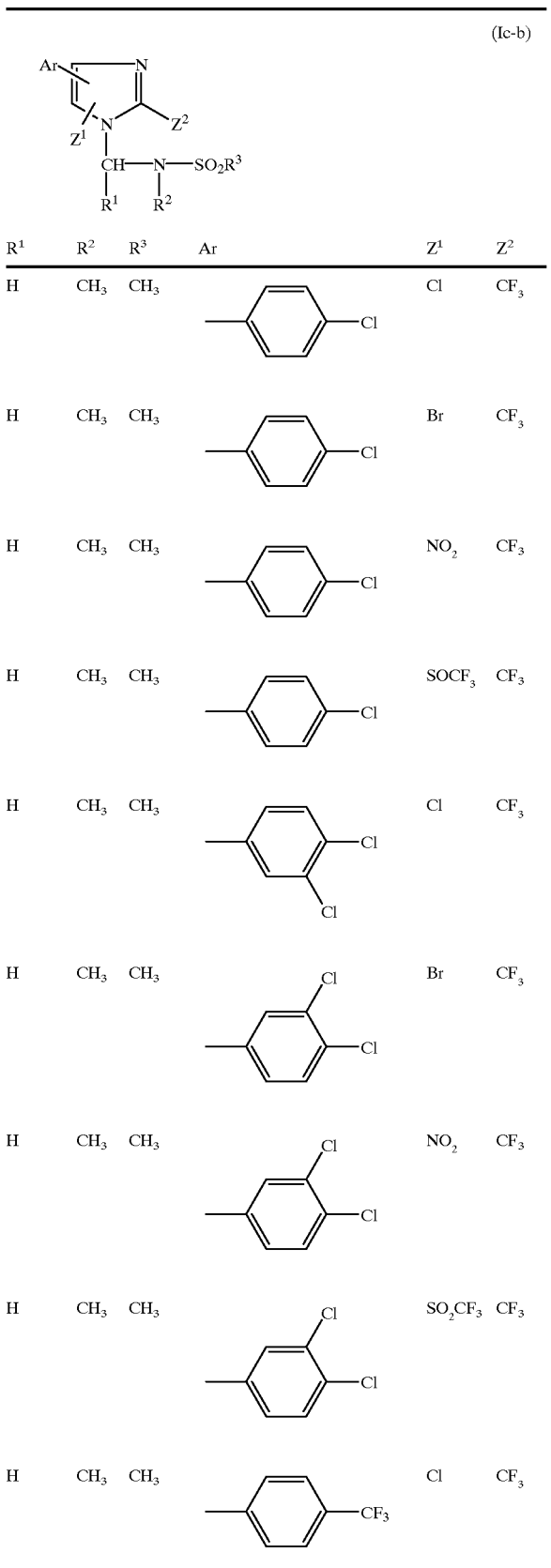
TABLE 3b-continued
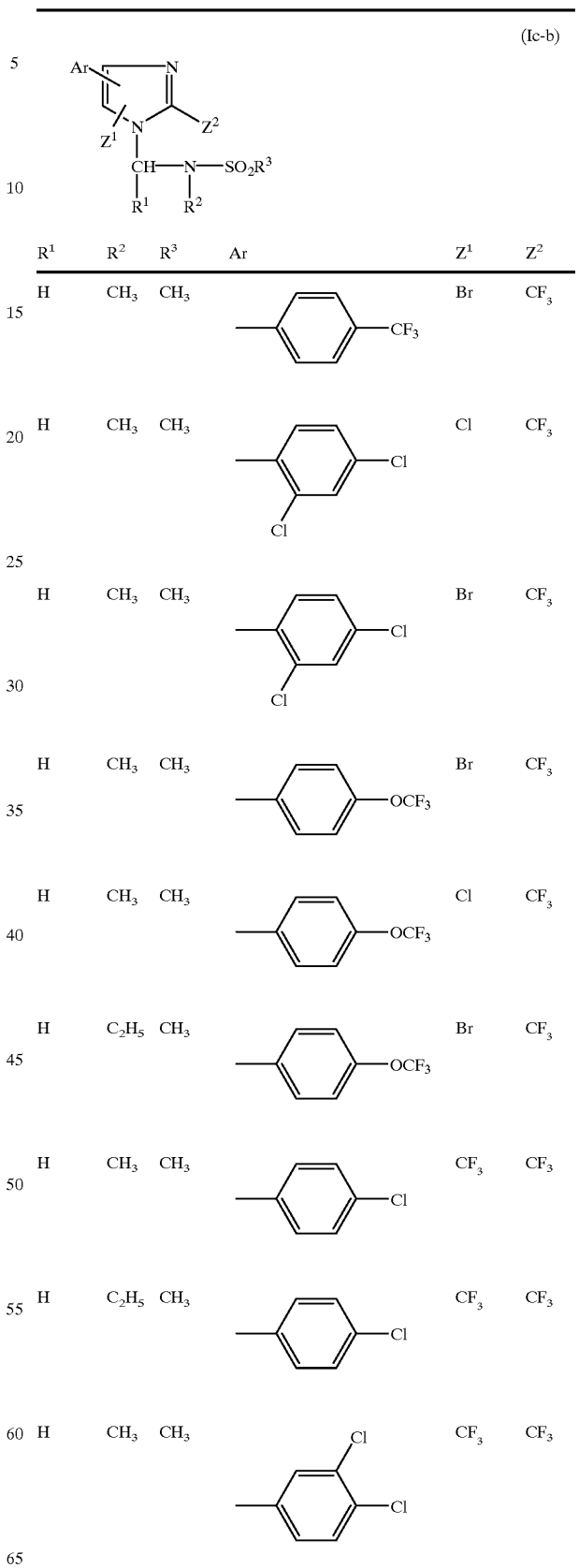

TABLE 3b-continued (Ic-b)

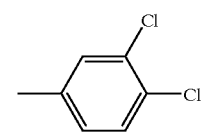

| R¹ | R² | R³ | Ar | Z¹ | Z² |
|---|---|---|---|---|---|
| H | C₂H₅ | CH₃ | (3,4-dichlorophenyl) | CF₃ | CF₃ |
| H | CH₃ | CH₃ | (4-trifluoromethylphenyl) | CF₃ | CF₃ |
| H | CH₃ | CH₃ | (4-trifluoromethoxyphenyl) | CF₃ | CF₃ |

TABLE 4

(Id)

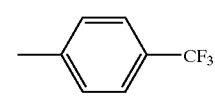

| R¹ | R² | R³ | R⁴ | X¹ | X² | X³ |
|---|---|---|---|---|---|---|
| H | CH₃ | CH₃ | CF₃ | H | Cl | Cl |
| H | CH₃ | Ph | CF₃ | H | Cl | Cl |
| H | Ph | CH₃ | CF₃ | H | Cl | Cl |
| H | CH₃ | CH₃ | CF₃ | H | Cl | H |
| H | Ph | CH₃ | CF₃ | H | Cl | H |
| H | CH₃ | Ph | CP3 | H | Cl | H |
| H | CH₃ | CH₃ | CF₃ | H | CF₃ | H |
| H | CH₃ | CH₃ | CF₃ | H | CF₃ | CF₃ |
| H | Ph | CH₃ | CF₃ | H | CF₃ | H |
| H | CH₃ | Ph | CF₃ | H | CF₃ | H |
| H | CH₃ | CH₃ | CF₃ | H | Br | Br |
| H | CH₃ | Ph | CF₃ | H | Br | Br |
| H | Ph | CH₃ | CF₃ | H | Br | Br |
| H | CH₃ | CH₃ | CHF₂ | H | Cl | H |
| H | CH₃ | CH₃ | CHF₂ | H | Br | H |
| H | (4-chlorophenyl) | CH₃ | CF₃ | H | Br | H |
| H | CH₃ | Ph | CF₃ | H | CF₃ | CF₃ |

TABLE 4-continued (Id)

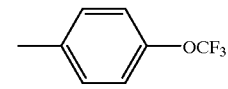

| R¹ | R² | R³ | R⁴ | X¹ | X² | X³ |
|---|---|---|---|---|---|---|
| H | Ph | CH₃ | CF₃ | H | CF₃ | CF₃ |
| H | CH₃ | CH₃ | CF₃ | H | NO₂ | H |

Using, for example, 2,4-bis-trifluoromethyl-6-bromobenzimidazole and N-chloromethyl-N-methyl-methanesulfonamide as starting materials, the course of reaction of the process according to the invention can be represented by the following equation:

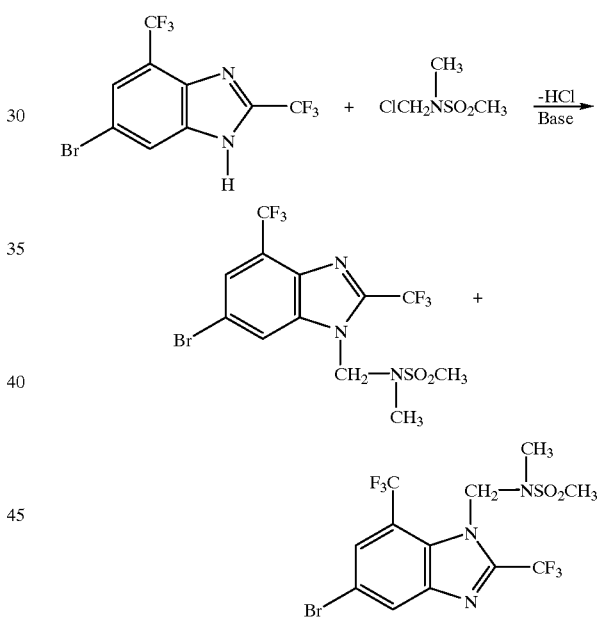

A general definition of the heterocycles required as starting materials for carrying out the process according to the invention is given by the formula (VI). The inclusion of the meanings given above for A results in the compounds of the formulae (VIa), (VIb), (VIc) and (VId)

(VIa)

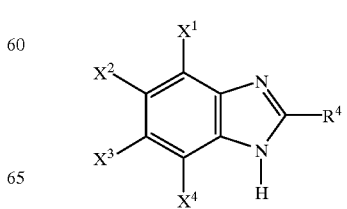

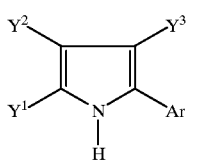
(VIb)

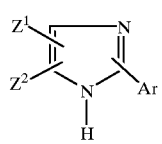
(VIc)

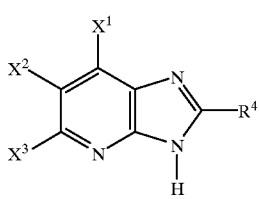
(VId)

in which

Ar, $X^1$, $X^2$, $X^3$, $X^4$, $Y^1$, $Y^2$, $Y^3$, $Z^1$, $Z^2$ and $R^4$ have the meanings given above.

A general definition of the 1H-benzimidazoles required as starting materials for carrying out the process according to the invention is given by the formula (VIa). In this formula (VIa), $R^4$, $X^1$, $X^2$, $X^3$ and $X^4$ preferably or particularly preferably represent those radicals which have already been mentioned, in connection with the description of the compounds of the formula (I) according to the invention, as being preferable or particularly preferable, respectively, for these substituents.

The 1H-benzimidazoles of the formula (VIa) are known or obtainable in analogy to known methods (cf. e.g. J. Am. Chem. Soc. 75, 1292 (1953); U.S. Pat. No. 3,576,818).

A general definition of the pyrroles required as starting materials for carrying out the process according to the invention is given by the formula (VIb). In this formula (VIb), Ar, $Y^1$, $Y^2$ and $Y^3$ preferably or particularly preferably represent those radicals which have already been mentioned, in connection with the description of the compounds of the formula (I) according to the invention, as being preferable or particularly preferable, respectively, for these substituents. The pyrroles of the formula (VIb) are known or obtainable in analogy to known methods (cf. e.g. J. Org. Chem. 43, 4278 (1978), EP 347 480, EP 426 948, U.S. Pat. No. 5,030,735, EP 549 866).

A general definition of the imidazoles required as starting materials for carrying out the process according to the invention is given by the formula (VIc). In this formula, Ar, $Z^1$ and $Z^2$ preferably or particularly preferably represent those radicals which have already been mentioned, in connection with the description of the compounds of the formula (I) according to the invention, as being preferred or particularly preferred for these substituents.

The imidazoles of the formula (VIc) are known or obtainable in analogy to known methods (cf. e.g. JP 02 262 560; U.S. Pat. No. 4,314,844; J. Heterocycl. Chem. 1973 10, 697; DE-A 2 155 558); they may be present as mixtures of regioisomers with respect to the position of the substituents in positions 4 and 5.

A general definition of the imidazopyridines required as starting materials for carrying out the process according to the invention is given by the formula (VId). In this formula (VId), $X^1$, $X^2$, $X^3$ and $R^4$ preferably or particularly preferably represent those radicals which have already been mentioned, in connection with the description of the compounds of the formula (I) according to the invention, as being preferable or particularly preferable, respectively, for these substituents.

The imidazopyridines of the formula (VId) are known or obtainable in analogy to known methods (cf. GB 1 114 199; JP 62 294 683; J. Heterocycl. Chem. 18, 303; EP 297 661; J. Med. Chem. 33, 2231).

A general definition of the alkylating agents also required as starting materials for carrying out the process according to the invention is given by the formula (VII).

In the formula (VII), $R^1$, $R^2$ and $R^3$ preferably or particularly preferably represent those radicals which have already been mentioned, in connection with the description of the substances of the formula (I) according to the invention, as being preferable or particularly preferable, respectively, for these substituents.

B preferably represents a leaving radical which is conventional in alkylating agents, and preferably represents halogen, and in particular represents chlorine, bromine or iodine or represents in each case optionally substituted alkylsulfonyloxy, alkoxysulfonyloxy or arylsulfonyloxy, such as, in particular, methanesulfonyloxy, trifluoromethanesulfonyloxy, methoxysulfonyloxy, ethoxysulfonyloxy or p-toluenesulfonyloxy.

B furthermore also represents an alcohol, alkanoyloxy or alkoxy group such as, for example, a hydroxyl, acetoxy or methoxy group.

The compounds of the formula (VIE) are known or obtainable in analogy to known methods (cf. e.g. Zh. Obshch. Khim. 56, 1429 (1986)).

Suitable diluents for carrying out the process according to the invention are inert organic solvents. These include, in particular, ariphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl or diethyl ether, ketones such as acetone, butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate, or bases such as pyridine, or organic acids such as formic acid or acetic acid.

The process according to the invention is preferably carried out in the presence of a suitable reaction auxiliary. Suitable such auxiliaries are all conventional inorganic or organic bases. These include, for example, alkaline earth metal or alkali metal hydrides, hydroxides, amides, alcoholates, acetates, carbonates or hydrogen carbonates, such as, for example, sodium hydride, sodium amide, lithium diethylamide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, organolithium compounds such as n-butyllithium, and tertiary amines such as trimethylamine, triethylamine, tributylamine, di-isopropyl-ethylamine, tetramethylguanidine, N,N'-dimethylaniline, pyridine, piperidine, N-methylpiperidine, N,N-dimethylaminopyridine, diazabicyclooctane (DABCO), diazabicyclononene (DBN) or diazabicycloundecene (DBU).

In cases where B in formula (VII) represents an alcohol, alkanoyloxy or alkoxy group, suitable reaction auxiliaries are also organic or inorganic acids, such as, for example, sulfuric acid, hydrochloric acid, p-toluenesulfonic acid, perfluorobutanesulfonic acid or strongly acid ion exchangers.

The process according to the invention can optionally also be carried out in a two-phase system such as, for example, water/toluene or water/dichloromethane, optionally in the presence of a suitable phase transfer catalyst. Examples of such catalysts which may be mentioned are: tetrabutylammonium iodide, tetrabutylammonium bromide, tetrabutylammonium chloride, tributyl-methyl-phosphoniumbromide, trimethyl-$C_{13}$/$C_{15}$-alkylammonium chloride, trimethyl-$C_{13}$/$C_{15}$-alkylammonium bromide, dibenzyldimethyl-ammonium methyl sulfate, dimethyl-$C_{12}$/$C_{14}$-alkyl-benzylammonium hydroxide, dimethyl-$C_{12}$/$C_{14}$-alkyl-benzylammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxyethoxy)ethyl]-amine.

When carrying out the process according to the invention the reaction temperatures can be varied over a relatively wide range. The process is in general carried out at temperatures of between −70° C. and +200° C., preferably at temperatures between 0° C. and 130° C.

The process according to the invention is normally carried out under atmospheric pressure. However, it is also possible to work under elevated or reduced pressure.

To carry out the process according to the invention, in general from 1.0 to 5.0 mol, preferably from 1.0 to 2.5 mol, of compound of the formula (VII) and, if appropriate, from 0.01 to 5.0 mol, preferably from 1.0 to 3.0 mol, of reaction auxiliary are employed per mole of compound of the formula (VIa), (VIb), (VIc) or (VId).

In a particular embodiment it is also possible in a preliminary reaction step first of all to silylate the compound of the formula (VIa), (VIb), (VIc) or (VId) with the aid of conventional methods of silylation, for example with hexamethyldisilazane or trimethylsilyl chloride, optionally in the presence of a suitable catalyst such as, for example, sulfuric acid, trifluoroacetic acid, ammonium sulfate, imidazole or saccharine, at temperatures of between −20° C. and +50° C., and in a second, subsequent step to react the 1-trimethylsilyl heterocycles which are obtainable in this way with alkylating agents of the formula (VII), in accordance with the process according to the invention. In this case it is advantageous to add tin tetrachloride as catalyst to the alkylation reaction (cf. e.g. Chem. Heterocycl. Comp. USSR 24, 514 (1988)).

The implementation of the reaction and the working-up and isolation of the reaction products are carried out by known methods (cf. in this respect also the Preparation Examples).

The end products of the formula (I) are purified with the aid of conventional methods, for example by column chromatography or by recrystallization.

Characterization is carried out by means of the melting point or, in the case of compounds which do not crystallize—especially in the case of mixtures of regioisomers—with the aid of proton nuclear magnetic resonance spectroscopy ($^1$H-NMR).

The active compounds are suitable for combating animal pests, preferably arthropods, in particular insects, which are encountered in agriculture, in forestry, in the protection of stored products and of materials, and in the hygiene field. They are active against normally sensitive and resistant species and against all or some stages of development.

The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp..

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Phylloxera vastatrix,* Pemphigus spp., *Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Caprocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp..

From the order of the Arachnida, for example, *Scorpio maurus* and *Latrodectus mactans*.

The compounds of the formula (I) according to the invention also exhibit a fungicidal action, for example against *Pyricularia oryzae* in rice, and an acaricidal action.

The active compounds can be converted to the customary formulations, such as solutions, emulsions, wettable powders, suspensions, powders, dusts, pastes, soluble powders and granules, suspension and emulsifiable concentrates, natural and synthetic materials impregnated with active compound, and very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water; by liquefied gaseous extenders or carriers are meant those liquids which are gaseous at ambient temperature and under atmospheric pressure, for example aerosol propellants, such as halogenated hydrocarbons as well as butane, propane, nitrogen and carbon dioxide; as solid carriers there are suitable:

for example, ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as albumen hydrolysis products; as dispersing agents there are suitable: for example lignin-sulfite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, attractants, sterilants, acaricides, nematicides, fungicides, growth-regulating substances or herbicides. The insecticides include, for example, phosphates, carbamates, carboxylates, chlorinated hydrocarbons, phenylureas, substances produced by microorganisms, etc.

The following compounds may be mentioned:

acrinathrin, alphamethrin, betacyfluthrin, bifenthrin, brofenprox, cis-resmethrin, clocythrin, cycloprothrin, cyfluthrin, cyhalothrin, cypermethrin, deltamethrin, esfenvalerate, etofenprox, fenpropathrin, fenvalerate, flucytlrinate, fluvalinate, lambdacyhalothrin, permethrin, pyresmethrin, pyrethrum, silafluofen, tralomethrin, zetamethrin.

alanycarb, bendiocarb, benfuracarb, bufencarb, butocarboxim, carbaryl, cartap, ethiofencarb, fenobucarb, fenoxycarb, isoprocarb, methiocarb, methomyl, metolcarb, oxamyl, pirimicarb, promecarb, propoxur, terbam, thiodicarb, thiofanox, trimethacarb, XMC, xylylcarb, acephate, azinphos A, azinphos M, bromophos A, cadusafos, carbophenothion, chlorfenvinphos, chlormephos, chlorpyrifos, chlorpyrifos M, cyanophos, demeton M, demeton-S-methyl, demeton S, diazinon, dichlorvos, dicliphos, dichlorfenthion, dicrotophos, dimethoate, dimethylvinphos, dioxathion, disulfoton, edifenphos, ethion, etrimphos, fenitrothion, fenthion, fonophos, formothion, heptenophos, iprobenfos, isazophos, isoxathion, phorate, malathion, mecarbam, mervinphos, mesulfenphos, methacrifos, methamidophos, naled, omethoate, oxydemeton M, oxydeprofos, parathion A, parathion M, phenthoate, phorate, phosalone, phosmet, phosphamidon, phoxim, pirimiphos A, pirimiphos M, propaphos, prothiophos, prothoate, pyraclophos, pyridaphenthion, quinalphos, salithion, sebufos, sulfotep, sulprofos, tetrachlorvinphos, temephos, thiomethon, thionazin, trichlorfon, triazophos, vamidothion, buprofezin, chlorfluazuron, diflubenzuron, flucycloxuron, flufenoxuron, hexaflumuron, pyriproxifen, tebufenozide, teflubenzuron, triflumuron, imidacloprid, nitenpyram, N-[(6-chloro-3-pyridyl)methyl]-N'-cyano-N-methylethaneimideamide (NI-25), abamectin, amitrazin, avermectin, azadirachtin, bensultap, bacillus thuringiensis, cyromazine, diafenthiuron, emamectin, ethofenprox, fenpyrad, fipronil, flufenprox, lufenuron, metaldehyde, milbemectin, pymetrozine, tebufenpyrad, triazuron, aldicarb, carbofuran, carbosulfan, chlorethoxyfos, cloethocarb, disulfoton, ethophrophos, etrimphos, fenamiphos, fipronil, fonofos, fosthiazate, furathiocarb, HCH, isazophos, isofenphos, methiocarb, monocrotophos, nitenpyram, oxamyl, prothiofos, pyrachlorfos, silafluofen, tebupirimphos, tefluthrin, terbufos, thiodicarb, thiafenox, azocyclotin, butylpyridaben, clofentezine, cyhexatin, diafenthiuron, diethion, emamectin, fenazaquin, fenbutatin oxide, fenothiocarb, fenpropathrin, fenpyrad, fenpyroximate, fluazinam, fluazuron, fluvalinate, fubfenprox, hexythiazox, ivemectin, methidathion, monocrotophos, moxidectin, profenofos, pyraclofos, pyridaben, pyrimidifen, tebufenpyrad, thuringiensin, triarathene and 4-bromo-2-(4-chlorophenyl)-1-(ethoxymethyl)-5-(trifluoromethyl)-1H-pyrrole-3-carbonitrile (AC 303630).

The active compounds according to the invention can furthermore be present in their commercially available formulations and in the use forms, prepared from these formulations, as a mixture with synergists. Synergists are compounds which increase the action of the active compounds without it being necessary for the synergist added to be active itself.

The active compound content of the use forms prepared from the commercially available formulations can vary within wide ranges. The active compound concentration of the use forms may be from 0.0000001 up to 95% by weight of active compound, preferably between 0.0001 and 1% by weight.

The compounds are employed in a customary manner appropriate to the use forms.

The preparation and use of the active compounds according to the invention is evident from the following examples.

PREPARATION EXAMPLES

Example Ia-1

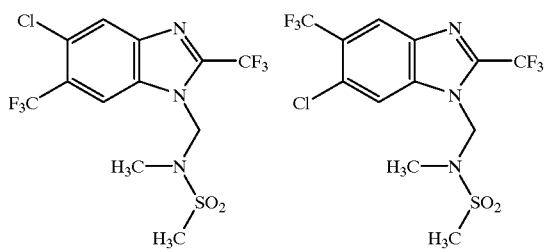

0.6 g (0.02 mol) of 80% pure sodium hydride is added in portions at 20° C. to 5.8 g (0.02 mol) of 6(5),2-bis-trifluoromethyl-5(6)-chlorobenzimidazole, in 50 ml of dimethylformamide. The mixture is heated at 40° C. until the end of the evolution of hydrogen. Then 3.2 g (0.02 mol) of N-chloromethyl-N-methylmethanesulfonamide in 10 ml of dimethylformamide are added dropwise at 20° C., and the mixture is heated at 80° C. for 6 hours. The reaction mixture is worked up by diluting it with water, extracting with ethyl acetate, drying the organic phase over sodium sulfate, concentrating it in vacuo and chromatographing the residue over silica gel (35 to 70 μm) with toluenelacetone (20:1). 5.0 g (61% of theory) of the compound of the above formula are obtained as a mixture of regioisomers in the ratio 3:2.

$^1$H-NMR (CDCl$_3$): δ=5.77 (s, 2H); 5.72 (s,2H) ppm (each NCH$_2$N).

In a corresponding manner, and in accordance with the general information on preparation, the following substituted benzimidazoles are obtained of the formula (Ia):

TABLE 5

(Ia)

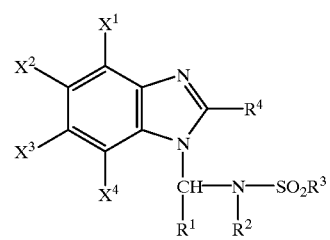

| Ex. No. | R$^1$ | R$^2$ | R$^3$ | R$^4$ | X$^1$ | X$^2$ | X$^3$ | X$^4$ | Physical Data |
|---|---|---|---|---|---|---|---|---|---|
| Ia-2 | H | CH$_3$ | CH$_3$ | CF$_3$ | CF$_3$ | H | Br | H | m.p. 167° C. |
| Ia-3 | H | CH$_3$ | CH$_3$ | CF$_3$ | SCF$_3$ | H | Br | H | m.p. 161° C. |
| Ia-4 | H | CH$_3$ | Ph** | CF$_3$ | CF$_3$ | H | Br | H | m.p. 132° C. |
| Ia-5 | H | CH$_3$ | Ph | CF$_3$ | SCF$_3$ | H | Br | H | m.p. 173° C. |
| Ia-6 | H | Ph | CH$_3$ | CF$_3$ | CF$_3$ | H | Br | H | m.p. 151° C. |
| Ia-7 | H | Ph | CH$_3$ | CF$_3$ | SCF$_3$ | H | Br | H | m.p. 121° C. |
| Ia-8 | H | C$_2$H$_5$ | CH$_3$ | CF$_3$ | SCF$_3$ | H | Br | H | m.p. 125° C. |
| Ia-9* | H | Ph | CH$_3$ | CF$_3$ | H | Cl | CF$_3$ | H | m.p. 167– |
|  | H | Ph | CH$_3$ | CF$_3$ | H | CF$_3$ | Cl | H | 171° C. |
| Ia-10* | H | CH$_3$ | Ph | CF$_3$ | H | Cl | CF$_3$ | H | m.p. 117– |
|  | H | CH$_3$ | Ph | CF$_3$ | H | CF$_3$ | Cl | H | 119° C. |
| Ia-11 | H | C$_2$H$_5$ | CH$_3$ | CF$_3$ | H | Cl | CF$_3$ | H | m.p. 120– |
|  | H | C$_2$H$_5$ | CH$_3$ | CF$_3$ | H | CF$_3$ | Cl | H | 123° C. |
| Ia-12* | H | | CH$_3$ | CF$_3$ | H | Cl | CF$_3$ | H | m.p. 210– |
|  | H | | CH$_3$ | CF$_3$ | H | CF$_3$ | Cl | H | 213° C. |

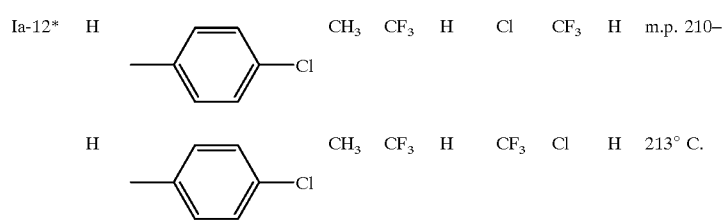

TABLE 5-continued

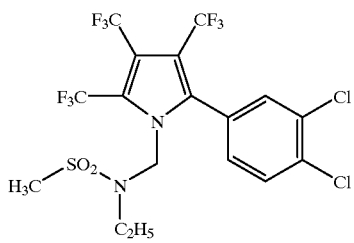

(Ia)

| Ex. No. | R¹ | R² | R³ | R⁴ | X¹ | X² | X³ | X⁴ | Physical Data |
|---------|----|----|----|----|----|----|----|----|---------------|

*Regioisomers
**Ph = phenyl

Preparation Example Ib-1

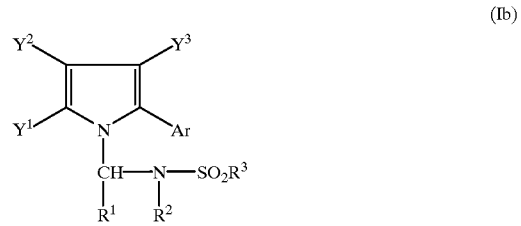

2.2 g (0.02 mol) of sublimed potassium tert-butylate are added at 20° C. to 8.3 g (0.02 mol) of 2-(3,4-dichlorophenyl)-3,4,5-tris-trifluoromethylpyrrole, in 100 ml of absolute tetrahydrofuran; a solution of 2.2 g (0.02 mol) of N-ethyl-N-chloromethylmethanesulfonamide in 10 ml of absolute tetrahydrofuran is added dropwise, and the mixture is stirred at 20° C. for 3 hours. The reaction mixture is discharged into 200 ml of water and extracted with methylene chloride, the organic phase is washed, dried over sodium sulfate and concentrated in vacuo, and the residue is chromatographed over silica gel (35 to 70 μm) with cyclohexane/ethyl acetate (3:1). 6.5 g (59% of theory) of the compound of the above formula are obtained.

$^1$H-NMR (CDCl$_3$): δ=2.75 (s, 3H)[CH$_3$SO$_2$—], 5.37 (s, 2H) ppm [NCH$_2$N].

In a corresponding manner, and in accordance with the general information on preparation, the following substituted pyrroles are obtained of the formula (Ib):

(Ib)

TABLE 6

| Ex. No. | R¹ | R² | R³ | Ar | Y³ | Y² | Y¹ | $^1$H-NMR (CDCl$_3$) [ppm], δ: |
|---------|----|----|----|----|----|----|----|-------------------------------|
| Ib-2 | H | CH$_3$ | Ph | ![3,4-dichlorophenyl] | Br | H | SO$_2$CClF$_2$ | 2.50 (s) 5.51 (s) 7.2–7.7 (m) |
| Ib-3 | H | Ph | CH$_3$ | ![benzodioxin-F4] | CN | Br | Br | 2.59 (s) 5.95 (s) 7.05–7.6 (m) |

TABLE 6-continued
| Ex. No. | R¹ | R² | R³ | Ar | Y³ | Y² | Y¹ | 1H-NMR (CDCl₃) [ppm], δ: |
|---|---|---|---|---|---|---|---|---|
| Ib-4 | H | Ph | CH₃ | 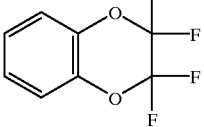 | CN | Br | Br | 2.95 (s) 5.95 (s) 7.00–7.70 (m) |
| Ib-5 | H | CH₃ | Ph | 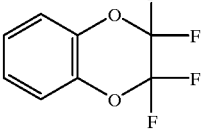 | CN | Br | Br | 2.55 (s) 5.29 (s) 7.2–7.7 (m) |
| Ib-6 | H | CH₃ | Ph | 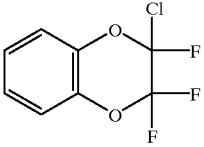 | CN | Br | Br | 2.55 (s) 5.30 (s) 7.2–7.7 (m) |
| Ib-7 | H | CH₃ | Ph | 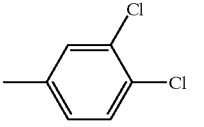 | CN | Br | CF₃ | 2.50 (s) 5.30 (s) 7.3–7.8 (m) |
| Ib-8 | H | CH₃ | CH₃ | 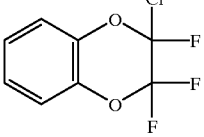 | CN | Br | Br | 2.65 (s) 2.75 (s) 5.45 (s) 7.2–7.7 (m) |
| Ib-9 | H | 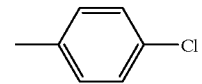 | CH₃ | 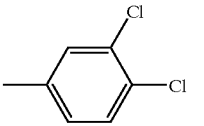 | CF₃ | CF₃ | CF₃ | 2.85 (s) 5.72 (s) AB-Spectrum m |
| Ib-10 | H | C₂H₅ | CH₃ | 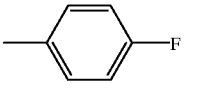 | CF₃ | CF₃ | CF₃ | 0.87 (s) 2.78 (s) 5.40 (s) |
| Ib-11 | H | C₂H₅ | CH₃ | 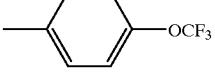 | CF₃ | CF₃ | CF₃ | 5.40 (s), 2.78 (s), 0.85 (t) |
| Ib-12 | H | C₂H₅ | CH₃ | 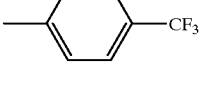 | CF₃ | CF₃ | CF₃ | 5.38 (s), 3.04 (q), 2.75 (s), |

TABLE 6-continued

| Ex. No. | R¹ | R² | R³ | Ar | Y³ | Y² | Y¹ | ¹H-NMR (CDCl₃) [ppm], δ: |
|---|---|---|---|---|---|---|---|---|
| Ib-13 | H | C₂H₅ | CH₃ | —⟨C₆H₄⟩—SCF₃ | CF₃ | CF₃ | CF₃ | 5.36 (s) 2.95 (q) 0.85 (t) |

Preparation Example Ic-1

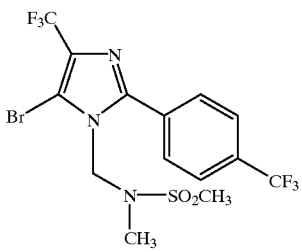

2.0 g (5.58 mmol) of 2-(4-trifluoromethylphenyl)-4(5)-trifluoromethyl-5(4)-bromoimidazole are dissolved in 20 ml of acetonitrile, and 1.0 g (6.14 mmol) of N-methyl-N-chloromethyl-methanesulfonamide and 1.5 g (11.0 mmol) of potassium carbonate are added. The reaction mixture is heated under reflux for 8 hours and filtered and the solvent is removed under reduced pressure. The residue is chromatographed over silica gel with dichloromethane as eluent, to give 1.3 g (45% of theory) of the compound of the above formula (and the isomer in respect of the position of the substituents in positions 4 and 5); melting point: 95 to 97° C.

In a corresponding manner, and in accordance with the general information on preparation, the following arylimidazoles are obtained of the formula (Ic):

TABLE 7

(Ic)

| Ex. No. | R¹ | R² | R³ | Ar | Z¹ | Z² | m.p. [° C.] or ¹H-NMR* (d₆-DMSO) [ppm] δ: |
|---|---|---|---|---|---|---|---|
| Ic-2 | H | CH₃ | CH₃ | 3,4-Cl₂-C₆H₃— | CF₃ | 2-CF₃ | 120–130 |
| Ic-3 | H | CH₃ | CH₃ | 4-Cl-C₆H₄— | Br | 2-CF₃ | 136–137 |
| Ic-4 | H | C₂H₅ | CH₃ | 3-Br-4-F-C₆H₃— | Br | 2-CF₃ | 2.94 (s) 3.30 (q) 5.69 (s) |

TABLE 7-continued
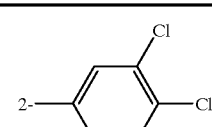
(Ic)
| Ex. No. | R¹ | R² | R³ | Ar | Z¹ | Z² | m.p. [° C.] or ¹H-NMR* (d₆-DMSO) [ppm] δ: |
|---|---|---|---|---|---|---|---|
| Ic-5 | H | CH₃ | CH₃ | 2-(3,4-dichlorophenyl) 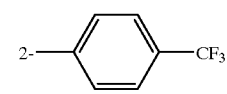 | CF₃ | CF₃ | 2.68 (s) 2.74 (s) 5.59 (s) |
| Ic-6 | H | CH3 | CH₃ | 2-(4-CF₃-phenyl) 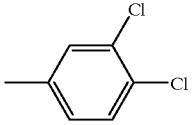 | CF₃ | CF₃ | 2.70 (s) 2.76 (s) 5.60 (s) |
| Ic-7 | H | CH₃ | CH₃ | 3,4-dichlorophenyl 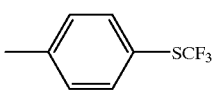 | 2-Br | CF₃ | 2.87 (s) 2.90 (s) 5.26 (s) |
| Ic-8 | H | CH₃ | CH₃ | 4-SCF₃-phenyl 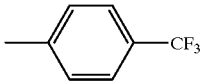 | 2-Br | CF₃ | 123–124 |
| Ic-9 | H | CH₃ | CH₃ | 4-CF₃-phenyl 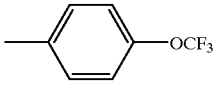 | Cl | 2-CF₃ | 112–113 |
| Ic-10 | H | CH₃ | CH₃ | 4-OCF₃-phenyl 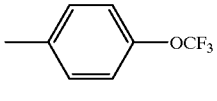 | 2-Cl | CF₃ | 2.37 (s) 2.74 (s) |
| Ic-11 | H | CH₃ | CH₃ | 4-OCF₃-phenyl 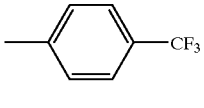 | 2-Br | CF₃ | 2.45 (s) 2.87 (s) 5.26 (s) |
| Ic-12 | H | CH₃ | CH₃ | 4-CF₃-phenyl 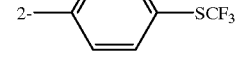 | 2-CN | CF₃ | 2.50 (s) 2.81 (s) 5.42 (s) |
| Ic-13 | H | CH₃ | CH₃ | 2-(4-SCF₃-phenyl) | Br | CF₃ | 2.59 (s) 2.61 (s) 5.61 (s) |

TABLE 7-continued (Ic)

| Ex. No. | R¹ | R² | R³ | Ar | Z¹ | Z² | m.p. [° C.] or ¹H-NMR* (d₆-DMSO) [ppm] δ: |
|---|---|---|---|---|---|---|---|
| Ic-14 | H | C₂H₅ | CH₃ | 2-─⟨⟩─SCF₃ | Br | CF₃ | 2.83 (s) 2.93 (q) 5.77 (s) |
| Ic-15 | H | CH₃ | CH₃ | 2-─⟨⟩(CF₃)(CF₃) | Br | CF₃ | 2.72 (s) 2.77 (s) 5.56 (s) |
| Ic-16 | H | C₂H₅ | CH₃ | 2-─⟨⟩─OC₂H₅ | Br | CF₃ | 2.84 (s) 2.97 (q) 5.79 (s) |

*of the main isomer

Preparation Example Id-1

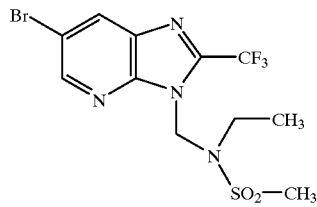

2.2 g (0.013 mol) of N-ethyl-N-chloromethylmethanesulfonamide in 10 ml dechloromethane are added dropwise over the course of about 10 minutes to a solution of 2.7 g (0.01 mol) of 6-bromo-2-trifluoromethyl-imidazole[4,5-b]pyridine and 1.8 ml (0.013 mol) of triethylamine in 100 ml of dichloromethane. The mixture is subsequently heated at reflux for 16 hours. After cooling, the reaction mixture is washed three times with water, the organic phase is dried over magnesium sulfate and the volatile components are stripped off in vacuo. The solid residue is chromatographed over silica gel with dichloromethane. 2.1 g (53% of theory) of the compound of the above formula are obtained; melting point: 158° C.

In a corresponding manner, and in accordance with the general information on preparation, the following substituted imidazopyridines are obtained of the formula (Id):

TABLE 8

(Id)

| Ex. No. | R¹ | R² | R³ | R⁴ | X¹ | X² | X³ | Physical Data |
|---|---|---|---|---|---|---|---|---|
| Id-2 | H | Ph | CH₃ | CF₃ | H | Br | H | m.p. 179° C. |
| Id-3 | H | CH₃ | Ph | CF₃ | H | Br | H | m.p. 140° C. |
| Id-4 | H | CH₃ | CH₃ | CF₃ | H | Br | H | m.p. 140° C. |

In the following Use Examples, the compounds (A) and/or (B) known from the prior art were employed as comparison substances.

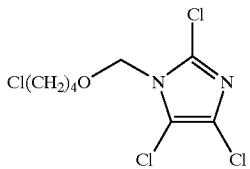

(A) known from JP 6 293 279

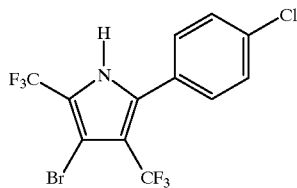

(B) known from EP 481 182

Use Examples

Example A

Phaedon larvae test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*) for as long as the leaves are still moist.

After the desired time, the destruction in % is determined. 100% means that all the beetle larvae have been killed; 0% means that none of the beetle larvae have been killed.

In this test, for example, the compounds of Preparation Examples Ia-1, Ia-2, Ia-11 and Ib-8 at an exemplary active compound concentration of 0.001% brought about a destruction of 100% after 3 days, whereas the compounds (A) and (B) known from the prior art did not bring about any destruction.

Example B

Plutella test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) for as long as the leaves are still moist.

After the desired time, the destruction in % is determined. 100% means that all the caterpillars have been killed; 0% means that none of the caterpillars have been killed.

In this test, for example, the compounds of Preparation Examples Ia-1, Ia-2, Ia-4, Ia-6, Ia-7, Ia-8, Ia-9, Ia-10, Ia-11, Ib-2, Ib-6, Ib-7, Ib-8 at an exemplary active compound concentration of 0.01% brought about a destruction of at least 85% after 7 days, whereas the comparison substance (A) brought about no destruction.

For example, the compounds of Preparation Examples Ia-1, Ia-10, Ib-2, Ib-7 and Ib-8 at an exemplary active compound concentration of 0.001% brought about a destruction of at least 85% after 7 days, whereas the comparison substance (B) brought about a destruction of only 10%.

Example C

Spodoptera test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Spodoptera frugiperda*) for as long as the leaves are still moist.

After the desired time, the destruction in % is determined. 100% means that all the caterpillars have been killed; 0% means that none of the caterpillars have been killed.

In this test, for example, the compounds of Preparation Examples Ia-1, Ia-9, Ia-10, and Ia-11 at an exemplary active compound concentration of 0.01% brought about a destruction of at least 90% after 7 days, whereas the compound (A) known from the prior art brought about a destruction of only 10%.

We claim:

1. An N-aryl or N-alkylsulfonylaminal of the formula

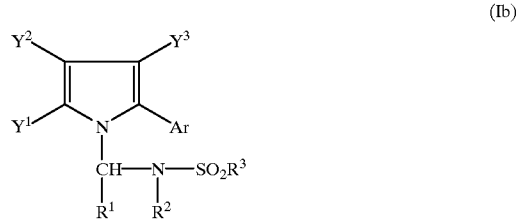

(Ib)

in which $R^1$ represents hydrogen, represents straight-chain or branched alkyl having 1 to 8 carbon atoms or represents optionally monosubstituted or polysubstituted phenyl wherein said substituents are halogen; cyano; nitro; in each case straight-chain or branched alkyl, alkoxy, alkylthio, alkylsulfinyl or alkylsulfonyl having in each case 1 to 6 carbon atoms; in each case straight-chain or branched halogenoalkyl, hatogenoalkoxy, halogenoalkylthio, halogenoalkylsulfinyl or hatogenoalkylsulfonyl having in each case 1 to 6 carbon atoms and 1 to 13 identical or different halogen atoms; in each case-straight-chain or branched alkoxyalkyl, alkoxyalkoxy, alkanoyl, alkoxycarbonyl or alkoxyiminoalkyl having in each case 1 to 6 carbon atoms in the individual alkyl moieties; divalent dioxyalkylene having 1 to 5 carbon atoms which Is optionally monosubstituted or polysubstituted by identical or different substituents selected from the group consisting of halogen, straight-chain or branched alkyl having 1 to 6 carbon atoms, straight-chain or branched halogenoalkyl having 1 to 6 carbon atoms and 1 to 13 identical or different halogen atoms; or phenyl which is optionally monosubstituted or polysubstituted by identical or different substituents selected from the group consisting of halogen, straight-chain or branched alkyl having 1 to 6 carbon atoms, or straight-chain or branched halogenoalkyl having 1 to 6 carbon atoms and 1 to 13 identical or different halogen atoms, $R^2$ and $R^3$ independently of one another represent straight-chain or branched alkyl having 1 to 8 carbon atoms or represent optionally monosubstituted or polysubstituted phenyl wherein said substituents are halogen; cyano; nitro; in each case straight-chain or branched alkyl, alkoxy, alkylthio, alkylsulfinyl or alkylsulfonyl having in each case 1 to 6 carbon atoms; in each case straight-chain or branched halogenoalkyl, halogenoalkylsulfonyl halogenoalkylthio, halogenoalkylsulfinyl or halogenoalkylsulfonyl having in each case 1 to 6 carbon atoms and 1 to 13 identical or different halogen atoms; in each case straight-chain or branched alkoxyalkyl, alkoxyalkoxy, alkanoyl, alkoxycarbonyl or alkoxyiminoalkyl having in each case 1 to 6 carbon atoms in the individual alkyl moieties; divalent dioxyalkylene having 1 to 5 carbon atoms which is optionally monosubstituted or polysubstituted by identical or different substituents selected from the group consisting of halogen, straight-chain or branched alkyl having 1 to 6 carbon atoms, or straight-chain or branched halogenoalkyl having 1 to 6 carbon atoms and 1 to 13 identical or different halogen atoms; or phenyl which is optionally monosubstituted or polysubstituted by identical or different substituents selected from the group consisting of halogen, straight-chain or branched alkyl having 1 to 6 carbon atoms, or straight-chain or branched halogenoalkyl having 1 to 6 carbon atoms and 1 to 13 identical or different halogen atoms, Ar represents phenyl which is optionally monosubstituted to pentasubstituted by identical or different substituents consisting of halogen, $C_1$–$C_8$-alkyl, $C_2$–$C_8$-alkenyl, and $C_2$–$C_8$-alkinyl, the alkyl, alkenyl or alkinyl radicals being optionally substituted by 1 to 6 radicals selected from the group consisting of chlorine, fluorine and bromine, or $C_1$–$C_5$-alkoxy which is optionally substituted by 1 to 6 halogen atoms, or $C_1$–$C_5$-thioalkyl which is optionally substituted by 1 to 6 radicals selected from the group consisting of chlorine, fluorine and bromine, or ($C_1$–$C_5$-alkyl)carbonyloxy, or divalent dioxyalklene having 1 to 5 carbon atoms which is optionally substituted by $C_1$–$C_8$-alkoxy, $C_2$–$C_8$-alkenoxy or $C_2$–$C_8$-alkinoxy, the alkoxy, alkenoxy or alkinoxy radicals being optionally substituted by 1 to 6 halogen atoms, or by $C_1$–$C_8$-thioalkyl, $C_2$–$C_8$-thioalkenyl or $C_2$–$C_8$-thioalkinyl, the thioalkyl, thioalkenyl orthioalkinyl radicals being optionally substituted by 1 to 6 substituents selected from the group consisting of chlorine, fluorine and bromine, or by ($C_1$–$C_8$-alkyl carbonyloxy which is optionally substituted by 1 to 6 halogen atoms, or by amino which is optionally substituted by 1 or 2 identical or different alkyl radicals having 1 to 8 carbon atoms, which are optionally substituted by 1 to 6 halogen atoms, or by nitro or cyano, or by 1 to 9 identical or different halogen atoms, $Y^1$, $Y^2$ and $Y^3$ independently of one another represent hydrogen, halogen, cyano, or nitro, represent $C_1$–$C_6$-alkyl which is optionally substituted by 1 to 8 identical or different halogen atoms, or represent $C_1$–$C_6$-alkylthio which is optionally substituted by halogen, represent $C_1$–$C_6$-alkylsulfinyl which is optionally substituted by halogen or represent $C_1$–$C_6$-alkylsulfonyl which is optionally substituted by halogen.

2. A compound according to claim 1, in which
$R^1$ represents hydrogen, represents straight-chain or branched alkyl having 1 to 6 carbon atoms or represents phenyl which is optionally monosubstituted or polysubstituted by identical or different substituents, wherein the substituents are:
halogen; cyano; nitro; In each case straight-chain or branched alkyl, alkoxy, alkylthio, alkylsulfinyl or alkylsulfonyl having in each case 1 to 4 carbon atoms, in each case straight-chain or branched halogenoalkyl, halogenoalkoxy, halogenoalkylthio, halogenoalkylsulfinyl or halogenoalkylsulfonyl having in each case 1 to 4 carbon atoms and 1 to 9 identical or different halogen atoms; in each case straight-chain or branched alkoxyalkyl, alkoxyalkoxy, alkanoyl, alkoxycarbonyl or alkoxyiminoalkyl having in each case 1 to 4 carbon atoms in the individual alkyl moieties; divalent dioxyalkylene having 1 to 4 carbon atoms which is optionally monosubstituted to hexasubstituted by identical or different substituents consisting of halogen, straight-chain or branched alkyl, having 1 to 4 carbon atoms, or straight-chain or branched halogenoalkyl having 1 to 4 carbon atoms and 1 to 9 identical or different halogen atoms; or phenyl which is optionally monosubstituted to pentasubstituted by identical or different substituents selected from the group consisting of halogen, straight-chain or branched alkyl having 1 to 4 carbon atoms or straight-chain or branched halogenoalkyl having 1 to 4 carbon atoms and 1 to 9 identical or different halogen atoms, $R^2$ and $R^3$ independently of one another represent straight-chain or branched alkyl having 1 to 6 carbon atoms or optionally monosubstituted to trisubstituted phenyl wherein said substituents are:
halogen; cyano; nitro- in each case straight-chain or branched alkyl, alkoxy, alkylthio, alkylsulfinyl or alkylsulfonyl having in each case 1 to 4 carbon atoms; in each case straight-chain or branched halogenoalkyl, halogenoalkoxy, halogenoalkylthio, halogenoalkylsulfinyl or halogenoalkylsulfonyl having in each case 1 to 4 carbon atoms and 1 to 9 identical or different halogen atoms; in each straight-chain or branched alkoxyalkyl, alkoxyalkoxy, alkanoyl, alkoxycarbonyl or alkoxyiminoalkyl having in each case 1 to 4 carbon atoms in the individual alkyl moieties; divalent dioxyalkylene having 1 to 4 carbon atoms which is optionally monosubstituted to hexasubstituted by identical or different substituents selected from the group consisting of halogen, straight-chain or branched alkyl having 1 to 4 carbon atoms, or straight-chain or branched halogenoalkyl having 1 to 4 carbon atoms and 1 to 9 identical or different halogen atoms; or phenyl which is optionally monosubstituted to pentasubstituted by identical or different substituents selected from the group consisting of halogen, straight-chain or branched alkyl having 1 to 4 carbon atoms, or straight-chain or branched halogenoalkyl having 1 to 4 carbon atoms and 1 to 9 identical or different halogen atoms;

$Y^1$, $Y^2$ and $Y^3$ independently of one another represent hydrogen, halogen, cyano, or nitro, represent $C_1$–$C_5$- alkyl which is optionally substituted by 1 to 6 identical or different halogen atoms, or represent $C_1$–$C_5$-alkylthio which is optionally substituted by halogen, represent $C_1$–$C_5$-alkylsulfinyl which is optionally substituted by halogen or represent $C_1$–$C_5$-alkylsulfonyl which is optionally substituted by halogen Ar represents phenyl which is optionally monosubstituted to tetrasubstituted by identical or different substituents consisting of fluorine, chlorine or bromine, $C_1$–$C_6$-alkyl, $C_2$–$C_6$-alkenyl, and $C_2$–$C_6$-alkinyl, the alkyl, alkenyl or alkinyl radicals being optionally substituted by 1 to 5 fluorine and/or chlorine atoms, or $C_1$–$C_4$-alkoxy which is optionally substituted by 1 to 5 fluorine and/or chlorine atoms, or $C_1$–$C_4$-thioalkyl which is optionally substituted by 1 to 5 fluorine and/or chlorine atoms, or ($C_1$–$C_4$-acyloxy, or divalent dioxyalkylene having 1 to 4 carbon atoms which is optionally substituted by $C_1$–$C_6$-alkoxy, $C_2$–$C_6$-alkenoxy or $C_2$–$C_6$-alkinoxy, the alkoxy, alkenoxy or alkinoxy radicals being optionally substituted by 1 to 5 fluorine and/or chlorine atoms, or by $C_1$–$C_6$-thioalkyl, $C_2$–$C_6$-thioalkenyl or $C_2$-$C_6$thioalkinyl, the thioalkyl, thioalkenyl or thioalkinyl radicals being optionally substituted by 1 to 5 fluorine and/or chlorine atoms, or by ($C_1$–$C_8$-alkyl)carbonyloxy which is optionally substituted by 1 to 5 fluorine and/or chlorine atoms, or by amino which is optionally substituted by 1 or 2 identical or different alkyl radicals having 1 to 6 carbon atoms, which are optionally substituted by 1 to 5 fluorine and/or chlorine atoms, or by nitro or cyano, or by 1 to 7 identical or different halogen atoms.

3. A compound according to claim 1, in which $R^1$ represents straight-chain or branched alkyl having 1 to 4 carbon atoms or represents optionally monosubstituted or disubstituted phenyl wherein said substituents are:

halogen; cyano; nitro; in each case straight-chain or branched alkyl, alkoxy, alkylthio, alkylsulfinyl or alkylsulfonyl having in each case 1 to 3 carbon atoms; in each case straight-chain or branched halogenoalkyl, halogenoalkoxy, halogenoalkylthio, halogenoalkylsulfinyl or halogenoalkylsulfonyl having in each case 1 to 3 carbon atoms and 1 to 7 identical or different halogen atoms; in each case straight-chain or branched alkoxyalkyl, alkoxyalkoxy, alkanoyl, alkoxycarbonyl or alkoxyiminoalkyl having in each case 1 to 3 carbon atoms in the individual alkyl moieties, divalent dioxyalkylene having 1 to 3 carbon atoms which is optionally monosubstituted to tetrasubstituted by identical or different substituents selected from the group consisting of halogen, straight-chain or branched alkyl having 1 to 3 carbon atoms, or straight-chain or branched halogenoalkyl having 1 to 3 carbon atoms and 1 to 7 identical or different halogen atoms; or phenyl which is optionally monosubstituted to trisubstituted by identical or different substituents selected from the group consisting of halogen, straight-chain or branched alkyl having 1 to 3 carbon atoms, or straight-chain or branched halogenoalkyl having 1 to 3 carbon atoms and 1 to 7 identical or different halogen atoms, $R^2$ and $R^3$ independently of one another represent straight-chain or branched alkyl having 1 to 4 carbon atoms or represents monosubstituted or disubstituted phenyl wherein said substituents are: halogen; cyano; nitro; in each case straight-chain or branched alkyl, alkoxy, alkylthio, alkylsulfinyl or alkylsulfonyl having in each case 1 to 3 carbon atoms; in each case straight-chain or branched halogenoalkyl, halogenoalkoxy, halogenoalkylthio, halogenoalkylsulfinyl or halogenoalkylsulfonyl having in each case 1 to 3 carbon atoms and 1 to 7 identical or different halogen atoms; in each case straight-chain or branched alkoxyalkyl, alkoxyalkoxy, alkanoyl, alkoxycarbonyl or alkoxyiminoalkyl having in each case 1 to 3 carbon atoms in the individual alkyl moieties; divalent dioxyalkylene having 1 to 3 carbon atoms which is optionally monosubstituted to tetrasubstituted by identical or different substituents selected from the group consisting of halogen, straight-chain or branched alkyl having 1 to 3 carbon atoms, or straight-chain or branched halogenoalkyl having 1 to 3 carbon atoms and 1 to 7 identical or different halogen atoms, or phenyl which is optionally monosubstituted to trisubstituted by identical or different substituents selected from the group consisting of halogen, straight-chain or branched alkyl having 1 to 3 carbon atoms, a straight-chain or branched halogenalkyl having 1 to 3 carbon atoms and 1 to 7 identical or different halogen atoms, Ar represents phenyl which is optionally monosubstituted to tetrasubstituted by identical or different substituents consisting of fluorine, chlorine or bromine, $C_1$–$C_4$-alkyl, $C_2$–$C_6$-alkenyl, and $C_2$–$C_6$-alkinyl, the alkyl, alkenyl or alkinyl radicals being optionally substituted by 1 to 5 fluorine and/or chlorine atoms, or $C_1$–$C_4$-alkoxy which is optionally substituted by 1 to 5 fluorine and/or chlorine atoms, or $C_1$–$C_4$-thioalkyl which is optionally substituted by 1 to 5 fluorine and/or chlorine atoms, or ($C_1$–$C_4$-acyloxy, divalent dioxyalkylene having 1 to 3 carbon atoms which is optionally substituted by $C_1$–$C_6$-alkoxy, $C_2$–$C_6$-alkenoxy or $C_2$–$C_6$-alkinoxy, the alkoxy, alkenoxy or alkinoxy radicals being optionally substituted by 1 to 5 fluorine and/or chlorine atoms, or by $C_1$–$C_4$-thioalkyl, $C_2$–$C_6$-thioalkenyl or $C_2$–$C_6$-thioalkinyl, the thioalkyl, thioalkenyl orthioalkinyl radicals being optionally substituted by 1 to 5 fluorine and/or chlorine atoms, or by ($C_1$–$C_5$-alkyl)carbonyloxy which is optionally substituted by 1 to 5 fluorine and/or chlorine atoms, or by amino which is optionally substituted by 1 or 2 identical or different alkyl radicals having 1 to 6 carbon atoms, which are optionally substituted by 1 to 5 fluorine and/or chlorine atoms, or by nitro or cyano, or by 1 to 5 identical or different halogen atoms.

4. An arthropodicidal composition which comprises an effective amount of a compound according to claim 1 and an inert carrier.

5. A method of combatting arthropods which comprises administering to said arthropods or to a habitat to which they reside an effective amount of a compound according to claim 1.

* * * * *